United States Patent
Knust et al.

(10) Patent No.: US 7,507,728 B2
(45) Date of Patent: Mar. 24, 2009

(54) HALOGEN SUBSTITUTED IMIDAZOL[1,5-A][1,2,4]TRIAZOLO[1,5-D][1,4]BENZODIAZEPINE DERIVATIVES

(75) Inventors: Henner Knust, Rheinfelden (DE); Andrew William Thomas, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 544 days.

(21) Appl. No.: 11/252,026

(22) Filed: Oct. 17, 2005

(65) Prior Publication Data
US 2006/0084801 A1     Apr. 20, 2006

(30) Foreign Application Priority Data
Oct. 20, 2004  (EP)  ............... 04105167

(51) Int. Cl.
A61P 25/28  (2006.01)
A61K 31/55  (2006.01)
C07D 243/00  (2006.01)

(52) U.S. Cl. ................. 514/219; 540/555
(58) Field of Classification Search ............. 514/219; 540/555
See application file for complete search history.

(56) References Cited

U.S. PATENT DOCUMENTS

| | | |
|---|---|---|
| 4,316,839 A | 2/1982 | Gerecke et al. |
| 4,772,599 A | 9/1988 | Wätjen |
| 4,775,671 A | 10/1988 | Hunkeler et al. |
| 4,897,392 A | 1/1990 | Tegeler et al. |
| 5,387,585 A | 2/1995 | Borer et al. |

FOREIGN PATENT DOCUMENTS

| | | |
|---|---|---|
| EP | 0 027 214 | 4/1981 |
| EP | 0 150 040 | 7/1985 |
| EP | 0 519 307 | 12/1992 |
| WO | WO 02/40487 | 5/2002 |
| WO | WO 02/094834 A1 | 11/2002 |

OTHER PUBLICATIONS

McNamara, et al., Psychobiology (1993), vol. 21(2) pp. 101-108.
Gerecke, et al., Heterocycles (1994), vol. 39, No. 2, pp. 693-721.
Breuer, Tetrahedron Letters (1976) No. 23, pp. 1935-1938.
Möhler et al., Nature (1981) vol. 294 pp. 763-765.
Möhler et al., Journal of Neurochemistry (1981), vol. 37(3), pp. 714-722.
Chemical Abstract 204054p, vol. 90, 1979, p. 624.
Chemical Abstract 37799s, vol. 108, 1988 p. 635.
Drug Evaluations, 6th Ed. (1986), American Medical Association, pp. 160-162.
Thompson et al., The New England Journal of Medicine (1990), vol. 323(7) pp. 445-448.
Rennie, Scientific American (1992) pp. 20 & 26.
Berkow et al., The Merck Manual of Diagnosis & Therapy, 15th Ed. (1987) pp. 839-840.
Wyngaarden, et al., Cecil Textbook of Medicine, 19th Ed. (1992), pp. 2075-2079.

*Primary Examiner*—Brenda L Coleman
(74) *Attorney, Agent, or Firm*—George W. Johnston; Patricia S. Rocha-Tramaloni; Kimberly J. Prior

(57) ABSTRACT

The invention relates to halogen substituted imidazo[1,5-a][1,2,4]triazolo[1,5-d][1,4]benzodiazepine derivatives of formula I

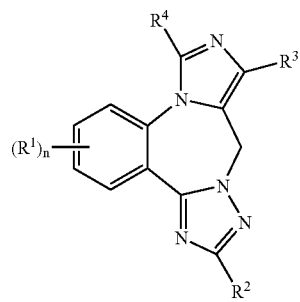

wherein
$R^1$, $R^2$, $R^3$, $R^4$ and n are as defined in the specification and to pharmaceutically acceptable acid addition salts thereof. The compounds can be used as a cognitive enhancer or for the treatment of cognitive disorders, anxiety, Alzheimer's disease and schizophrenia.

26 Claims, No Drawings

HALOGEN SUBSTITUTED IMIDAZOL[1,5-A][1,2,4]TRIAZOLO[1,5-D][1,4]BENZODIAZEPINE DERIVATIVES

BACKGROUND OF THE INVENTION

It has been found that this class of compounds show high affinity and selectivity for GABA A α5 receptor binding sites and might be useful as cognitive enhancer or for the treatment of cognitive disorders, anxiety, schizophrenia or Alzheimer's disease.

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology*, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides halogen substituted imidazo[1,5-a][1,2,4]triazolo[1,5-d][1,4]benzodiazepine derivatives of formula I

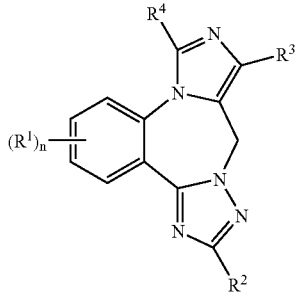

I wherein
$R^1$ is hydrogen, halogen, lower alkyl, $Si(CH_3)_3$, lower alkyl substituted by halogen, lower alkoxy, lower alkoxy substituted by halogen, lower alkenyl, lower alkenyloxy, CN, bicyclo[2.2.1]hept-5-en-2-yl, aryl which is optionally substituted by lower alkyl, amino or lower alkoxy, or is aryloxy, heteroaryl, benzo[1,3]dioxolyl, cydoalkyl, heterocycloalkyl, $-O(CH_2)_mOH$, $-CO(O)$-lower alkyl, $-N(R')_2$ or $-C\equiv C-R''$;
R' is hydrogen, lower alkyl, cycloalkyl, $-C(O)$-lower alkyl, $-C(O)$-cycloalkyl, $-S(O)_2$-lower alkyl, or aryl which is unsubstituted or substituted by one or two substituents selected from the group consisting of halogen and lower alkyl substituted by halogen;
R" is hydrogen, $-Si(CH_3)_3$, lower alkyl, cycloalkyl or $-(CH_2)_m$-O-lower alkyl;
$R^2$ is hydrogen, methyl or aryl;
$R^3$ is halogen;
$R^4$ is hydrogen or halogen;
n is 1 or 2; and
m is 1, 2 or 3;

and pharmaceutically acceptable acid addition salts thereof.

The invention also provides pharmaceutical compositions which comprise a therapeutically effective amount of a compound of the invention and a pharmaceutically acceptable carrier.

This class of compounds have a high affinity and selectivity for GABA A α5 receptor binding sites. Therefore, the invention further provides methods for enhancing cognition and for the treatment of cognitive disorders, anxiety, schizophrenia, and Alzheimer's disease. The most preferred indication in accordance with the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain alkyl group containing from 1-7, preferably from 1-4 carbon atoms, for example, methyl, ethyl, propyl, isopropyl, n-butyl, i-butyl, t-butyl and the like.

The term "halogen" denotes chlorine, iodine, fluorine and bromine.

The term "lower alkyl substituted by halogen" denotes a lower alkyl group as defined above, wherein at least one hydrogen atom is replaced by a halogen atom. Examples of preferred groups are $CF_3$, $CHF_2$, $CH_2F$, $CH_2CH_2F$, $CH_2CF_2H$, or $CH_2CF_3$ or $CF_2CH_3$.

The term "lower alkoxy" denotes a group wherein the alkyl residue is as defined above that is attached via an oxygen atom. Examples for lower alkoxy include methoxy, ethoxy and propoxy.

The term "lower alkoxy substituted by halogen" denotes a lower alkoxy group as defined above, wherein at least one hydrogen atom on the alkyl residue is replaced by a halogen atom. An example of a lower alkoxy substituted by halogen is trifluoromethoxy.

The term "lower alkenyl" denotes a straight- or branched-chain carbon group containing from 2-7, preferably from 2-4 carbon atoms, wherein at least one bond is a double bond The term "lower alkenyloxy" denotes a group wherein the alkenyl residue is as defined above that is attached via an oxygen atom.

The term "aryl" denotes a phenyl, benzyl or naphthyl group. Preferred groups are phenyl or benzyl.

The term "aryloxy" denotes an aryl group as defined above that is attached via an oxygen atom.

The term "heteroaryl" denotes an aromatic 5 or 6 membered ring containing from one to three heteroatoms, such as N, O or S atoms. Examples of such heteroaryl groups are imidazole or pyridine.

The term "cycloalkyl" denotes a cyclic alkyl ring having from 3 to 7 carbon ring atoms, for example, cyclopropyl, cyclopentyl or cyclohexyl.

The term "heterocycloalkyl" denotes a cyclic alkyl ring, having from 3 to 7 carbon ring atoms wherein one to three of the ring carbon atoms is replaced by a heteroaom, such as N, O or S, for example the following groups: morpholine, thiomorpholine, piperazine, piperidine and the like.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides halogen substituted imidazo[1,5-a][1,2,4]triazolo[1,5-d][1,4]benzodiazepine derivatives of formula I

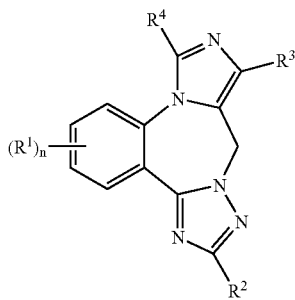

wherein
$R^1$ is hydrogen, halogen, lower alkyl, $Si(CH_3)_3$, lower alkyl substituted by halogen, lower alkoxy, lower alkoxy substituted by halogen, lower alkenyl, lower alkenyloxy, CN, bicyclo[2.2.1]hept-5-en-2-yl, aryl which is optionally substituted by lower alkyl, amino or lower alkoxy, or is aryloxy, heteroaryl, benzo[1,3]dioxolyl, cycloalkyl, heterocycloalkyl, $—O(CH_2)_mOH$, $—CO(O)$-lower alkyl, $—N(R')_2$ or $—C\equiv C—R''$;
R' is hydrogen, lower alkyl, cycloalkyl, —C(O)-lower alkyl, —C(O)-cydoalkyl, —S(O)$_2$-lower alkyl, or aryl which is unsubstituted or substituted by one or two substituents selected from the group consisting of halogen and lower alkyl substituted by halogen;
R'' is hydrogen, —Si(CH$_3$)$_3$, lower alkyl, cycloalkyl or —(CH$_2$)$_m$—O-lower alkyl;
$R^2$ is hydrogen, methyl or aryl;
$R^3$ is halogen;
$R^4$ is hydrogen or halogen;
n is 1 or 2; and
m is 1, 2 or 3;

and pharmaceutically acceptable acid addition salts thereof.

Exemplary preferred are compounds are those which have a binding activity (Ki) of lower than 15 nM and are selective for GABA A α5 subunits and are relatively free of activity at GABA A α1, α2 and α3 receptor binding sites.

Preferred compounds of formula I are those, in which $R^3$ chlorine.

Most preferred compounds from this group are those, wherein $R^2$ is hydrogen, for example the following compounds:

10-chloro-9H-imidazo[1,5-a][1,2,4]triazolo[1,5-d][1,4]benzodiazepine,
10-chloro-3-fluoro-9H-imidazo[1,5-a][1,2,4]triazolo[1,5-d][1,4]benzodiazepine,
10-chloro-3-methoxy-9H-imidazo[1,5-a][1,2,4]triazolo[1,5-d][1,4]benzodiazepine,
10-chloro-3-ethoxy-9H-imidazo[1,5-a][1,2,4]triazolo[1,5-d][1,4]benzodiazepine,
10-chloro-3-(2-fluoro-ethoxy)-9H-imidazo[1,5-a][1,2,4]triazolo[1,5-d][1,4]benzodiazepine,
10-chloro-3-(2,2-difluoro-ethoxy)-9H-imidazo[1,5-a][1,2,4]triazolo[1,5-d][1,4]benzodiazepine,
10-chloro-3-(2,2,2-trifluoro-ethoxy)-9H-imidazo[1,5-a][1,2,4]triazolo[1,5-d][1,4]benzodiazepine,
10-chloro-3-vinyloxy-9H-imidazo[1,5-a][1,2,4]triazolo[1,5-d][1,4]benzodiazepine,
10-chloro-3-methylamino-9H-imidazo[1,5-a][1,2,4]triazolo[1,5-d][1,4]benzodiazepine,
10-chloro-3-dimethylamino-9H-imidazo[1,5-a][1,2,4]triazolo[1,5-d][1,4]benzodiazepine,
3-benzylamino-10-chloro-9H-imidazo[1,5-a][1,2,4]triazolo[1,5-d][1,4]benzodiazepine,
10-chloro-3-thiomorpholin-4-yl-9H-imidazo[1,5-a][1,2,4]triazolo[1,5-d][1,4]benzodiazepine,
10-chloro-3-imidazol-1-yl-9H-imidazo[1,5-a][1,2,4]triazolo[1,5-d][1,4]benzodiazepine,
3-acetylamino-10-chloro-9H-imidazo[1,5-a][1,2,4]triazolo[1,5-d][1,4]benzodiazepine,
3,10-dichloro-9H-imidazo[1,5-a][1,2,4]triazolo[1,5-d][1,4]benzodiazepine,
3-bromo-10-chloro-9H-imidazo[1,5-a][1,2,4]triazolo[1,5-d][1,4]benzodiazepine,
10-chloro-3-methyl-9H-imidazo[1,5-a][1,2,4]triazolo[1,5-d][1,4]benzodiazepine,
10-chloro-3-ethynyl-9H-imidazo[1,5-a][1,2,4]triazolo[1,5-d][1,4]benzodiazepine,
10-chloro-3-prop-1-ynyl-9H-imidazo[1,5-a][1,2,4]triazolo[1,5-d][1,4]benzodiazepine,
10-chloro-3-cyclopropylethynyl-9H-imidazo[1,5-a][1,2,4]triazolo[1,5-d][1,4]benzodiazepine,
10-chloro-3-ethyl-9H-imidazo[1,5-a][1,2,4]triazolo[1,5-d][1,4]benzodiazepine,
10-chloro-3-cydopropyl-9H-imidazo[1,5-a][1,2,4]triazolo[1,5-d][1,4]benzodiazepine,
10-chloro-3-difluoromethyl-9H-imidazo[1,5-a][1,2,4]triazolo[1,5-d][1,4]benzodiazepine,
3-benzyl-10-chloro-9H-imidazo[1,5-a][1,2,4]triazolo[1,5-d][1,4]benzodiazepine,
10-chloro-3-phenyl-9H-imidazo[1,5-a][1,2,4]triazolo[1,5-d][1,4]benzodiazepine, 10-chloro-3-cyano-9H-imidazo[1,5-a][1,2,4]triazolo[1,5-d][1,4]benzodiazepine,
10-chloro-3-(pyridin-3-yl)-9H-imidazo[1,5-a][1,2,4]triazolo[1,5-d][1,4]benzodiazepine,
10-chloro-3-propyl-9H-imidazo[1,5-a][1,2,4]triazolo[1,5-d][1,4]benzodiazepine,
3-butyl-10-chloro-9H-imidazo[1,5-a][1,2,4]triazolo[1,5-d][1,4]benzodiazepine,
10-chloro-3-vinyl-9H-imidazo[1,5-a][1,2,4]triazolo[1,5-d][1,4]benzodiazepine,
10-chloro-3-(methoxy-carbonyl)-9H-imidazo[1,5-a][1,2,4triazolo1,5-d][1,4]benzodiazepine,
10-chloro-3-(propa-1,2-dienyl)-9H-imidazo[1,5-a][1,2,4]triazolo[1,5-d][1,4]benzodiazepine,
3-(cyclopropanecarbonyl-amino)-10-chloro-9H-imidazo[1,5-a][1,2,4]triazolo[1,5-d][1,4]benzodiazepine, and
0-chloro-3-cyclopropylamino-9H-imidazo[1,5-a][1,2,4]triazolo[1,5-d][1,4]benzodiazepine.

Further preferred compounds from this group are those, wherein $R^2$ is methyl, for example the following compounds:
3,10-dichloro-6-methyl-9H-imidazo[1,5-a][1,2,4]triazolo[1,5-d][1,4]benzodiazepine,
3-bromo-10-chloro-6-methyl-9H-imidazo[1,5-a][1,2,4]triazolo[1,5-d][1,4]benzodiazepine,
10-chloro-3-ethynyl-6-methyl-9H-imidazo[1,5-a][1,2,4]triazolo[1,5-d][1,4]benzodiazepine,
10-chloro-3-cydopropyl-6-methyl-9H-imidazo[1,5-a][1,2,4]triazolo[(1,5-d][1,4]benzodiazepine, and
10-chloro-3-cyano-6-methyl-9H-imidazo[1,5-a][1,2,4]triazolo[1,5-d][1,4]benzodiazepine.

Preferred compounds of formula I are further those, in which $R^3$ bromine, for example the following compounds:
10-bromo-9H-imidazo[1,5-a][1,2,4]triazolo[1,5-d][1,4]benzodiazepine and
10-bromo-3-fluoro-9H-imidazo[1,5-a][1,2,4]triazolo[1,5-d][1,4]benzodiazepine.

Preferred compounds of formula I are further those, in which $R^3$ iodine, for example the following compound:
3-chloro-10-iodo-9H-imidazo[1,5-a][1,2,4]triazolo[1,5-d][1,4]benzodiazepine.

In another embodiment, the invention provides compounds of formula IA

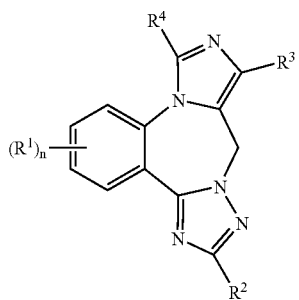

IA wherein
$R^1$ is hydrogen, halogen, lower alkyl, lower alkyl substituted by halogen, lower alkoxy, lower alkoxy substituted by halogen, lower alkenyl, lower alkenyloxy, CN, aryl, aryloxy, heteroaryl, cycloalkyl, heterocycloalkyl, —O(CH$_2$)$_m$OH, —N(R')$_2$ or —C≡C—R";
R' is hydrogen, lower alkyl, —C(O)—lower alkyl, —C(O)-cycloalkyl, —S(O)$_2$-lower alkyl, or aryl which is unsubstituted or substituted by one or two substituents selected from the group consisting of halogen and lower alkyl substituted by halogen;
R" is hydrogen, —Si(CH$_3$)$_3$, lower alkyl, cycloalkyl or —(CH$_2$)$_m$—O-lower alkyl;
$R^2$ is hydrogen, methyl or aryl;
$R^3$ is halogen;
$R^4$ is hydrogen or halogen;
n is 1 or 2; and
m is 1, 2 or 3;

and pharmaceutically acceptable acid addition salts thereof.

The present compounds of formula I and their pharmaceutically acceptable salts may be prepared by methods known in the art, for example, by processes described below, which processes comprise reacting a compound of formula

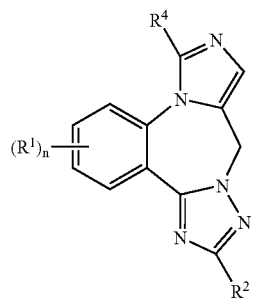

II with a halogenating agent, such as N-chlorosuccinimide, 1,3-dichloro-5,5-dimethylhydantoin, bromine or iodine, to produce a compound of formula

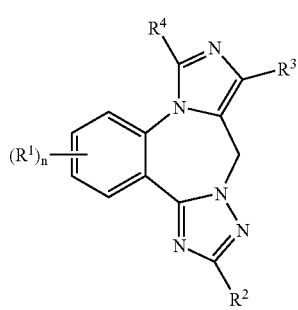

I wherein $R^1$, $R^2$, $R^3$, $R^4$ and n are as described above, and, if desired, converting the compound of formula I into a pharmaceutically acceptable salt. In accordance with the present invention, compounds of the general formula I can be prepared as follows: a compound of formula II can be halogenated by an appropriate reagent, for example N-chlorosuccinimide, N-bromosuccinimide, iodine or the like, in a suitable solvent to afford a compound of formula I.

The following schemes (scheme 1-4) describe the processes for preparation of compounds of formula I in more detail. The starting materials are known compounds or may be prepared according to methods known in the art.

Scheme 1

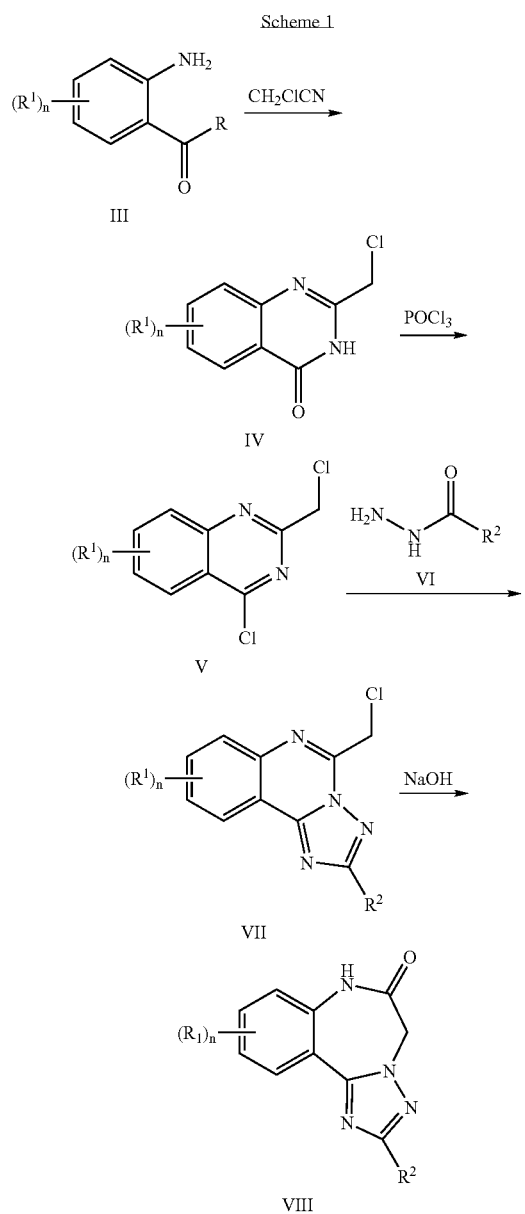

R = OH, alkoxy, amino

In accordance with scheme 1, a corresponding intermediate compound of formula VIII is known (EP 519 307) and may be prepared by methods, known in the art, for example in the following way.

A corresponding compound of formula III, an $R^1$-substituted 2-aminobenzoic acid derivative, and chloroacetonitrile is dissolved in dioxane, and a weak stream of dry HCl is introduced at 5° C. to 15° C. for a period of several hours. After addition of further chloroacetonitrile, the mixture is stirred at ambient temperature for several hours. The obtained compound of formula IV is purified in conventional manner and dissolved in chloroform in the presence of N,N-dimethyl-p-toluidine. Phosphorous oxide chloride is added, and the solution heated. The obtained compound of formula V is purified by known methods and heated with a compound of formula VI, an acylhydrazide, in toluene for several hours affording a compound of formula VII, for example the compound 5-chloromethyl-9-fluoro-1,2,4-triazolo[4,3-c] quinazoline. Finally, a compound of formula VIII is obtained by dissolving a compound of formula VII in dioxane and treating with aqueous sodium hydroxide such that the reaction temperature is between 10° C. to 15° C. Conventional workup and purification affords a corresponding intermediate of formula VIII, for example 10-fluoro-5H-[1,2,4]triazolo[1,5-d][1,4]benzodiazepin-6(7H)-one.

Scheme 2

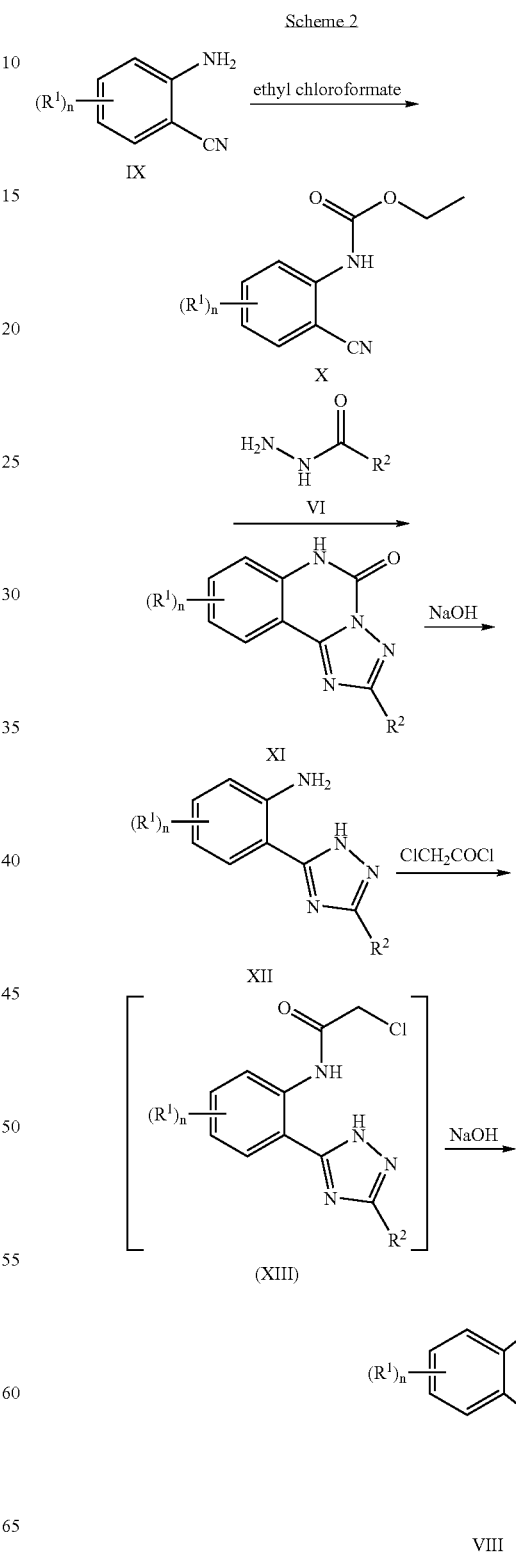

In accordance with scheme 2, a corresponding intermediate compound of formula VIII may be prepared alternatively in the following way:

A corresponding compound of formula IX, an R¹-substituted 2-aminobenzonitrile, is heated with ethyl chloroformate to obtain a carbamic acid ester of formula X, which is treated with a compound of formula VI, an acylhydrazide, in 1-methyl-2-pyrrolidone at 160° C. under removal of ethanol. Conventional workup provides a urea of formula XI which is heated with aqueous sodium hydroxide in ethylenglycol to obtain a compound of formula XII. Treatment of a compound of formula XII with chloroacetyl chloride in acetic acid provides an amide of formula XIII, which is treated with aqueous sodium hydroxide in dioxane at ambient temperature to obtain the intermediate of formula VIII. Alternatively, a compound of formula XII can be directly transformed to a compound of formula VIII by dissolving a compound of formula XII in dioxane and pyridine and adding dropwise chloroacetyl chloride at a temperature between 10° C. to 15° C. After stirring for a short period of time aqueous sodium hydroxide is added and the reaction mixture stirred for several hours at ambient temperature to obtain the compound of formula VIII.

is isolated in conventional manner or directly used in the next reaction step. Finally, a compound of formula X is obtained by the reaction of IX with a mixture of a cooled solution of lithium diisopropylamide or lithium hexamethyldisilazide in THF and (E)-(dimethylamino-methylenamino)-acetic acid ethyl ester or with a mixture of a cooled solution of ethyl isocyanoacetate in THF and potassium tert-butoxide or sodium hydride.

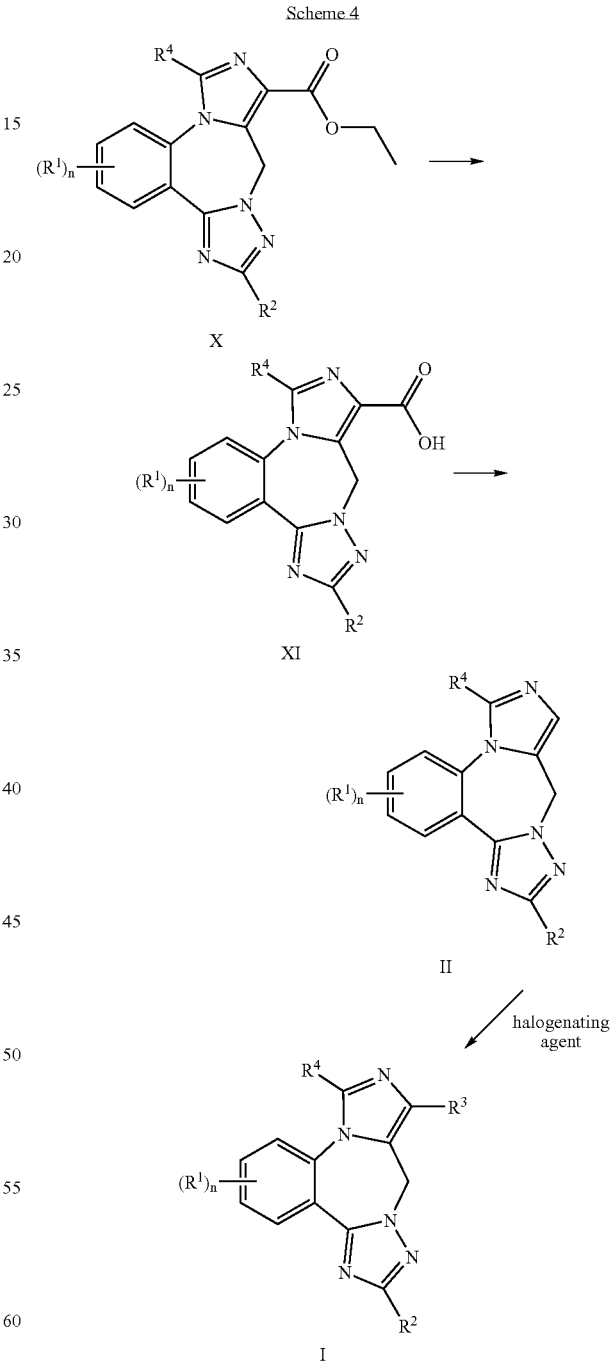

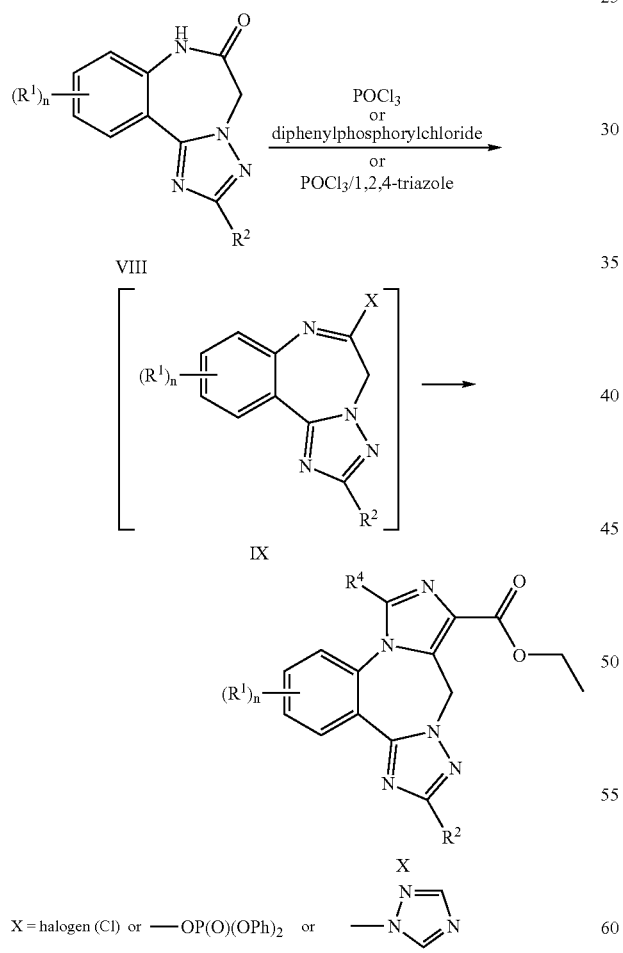

In accordance with scheme 3, a compound of formula VIII is treated with an activation agent in the presence of base at elevated temperature, for example phosphorous oxide chloride in toluene or chloroform in the presence of N,N-dimethyl-p-toluidine, to obtain a compound of formula IX which According to scheme 4, a compound of formula X is hydrolyzed to the corresponding carboxylic acid XI, for example by treatment with sodium hydroxide in ethanol at elevated temperature. Decarboxyation of a compound of formula XI to a compound of formula II can be achieved by stirring in an appropriate solvent, for example diethylene glycol dibutyl ether, at elevated temperature, for example 200° C. or the like, for some time. Finally, a compound of formula II can be halogenated to a compound of formula I by reaction with an appropriate halogenation reagent, for example N-chlorosuccinimide or 1,3-dichloro-5,5-dimethylhydantoin, bromine, iodine or the like, in an appropriate solvent, for example N,N-dimethylformamide or dichloromethane or the like, at ambient or elevated temperature.

As mentioned earlier, the compounds of formula I and their pharmaceutically usable salts possess valuable pharmacological properties. The compounds of the present invention are ligands for GABA A receptors containing the α5 subunit and are therefore useful in the therapy where cognition enhancement is required.

The compounds were investigated in accordance with the test given hereinafter.

MEMBRANE PREPARATION AND BINDING ASSAY

The affinity of compounds at GABA A receptor subtypes was measured by competition for [$^3$H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl$_2$, 1.2 mM MgCl$_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 µL (96-well plates) which contained 100 µL of cell memebranes, [$^3$H]flumazenil at a concentration of 1 nM for α1, α2, α3 subunits and 0.5 nM for α5 subunits and the test compound in the range of $10^{-10}$–$3\times10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and all were found to possess a Ki value for displacement of [$^3$H]flumazenil from α5 subunits of the rat GABA A receptor of 100 nM or less. In a preferred embodiment the compounds of the invention are binding selective for the α5 subunit relative to the α1, α2 and α3 subunit.

In the table below it is shown the activity data of some preferred compounds:

| Example No. | Ki[nM] hα1 | Ki[nM] hα2 | Ki[nM] hα3 | Ki[nM] hα5 |
|---|---|---|---|---|
| 1 | 3.8 | 1.5 | 0.7 | 0.3 |
| 2 | 0.7 | 1.2 | 0.78 | 0.3 |
| 3 | 12.2 | 17.2 | 11.7 | 0.8 |

-continued

| Example No. | Ki[nM] hα1 | Ki[nM] hα2 | Ki[nM] hα3 | Ki[nM] hα5 |
|---|---|---|---|---|
| 7 | 18.5 | 25.0 | 20.7 | 1.3 |
| 8 | 22.1 | 29.4 | 24.4 | 2.0 |
| 10 | 22.4 | 25.6 | 11.4 | 1.2 |
| 12 | 5.9 | 15.7 | 8.0 | 1.8 |
| 21 | 33.0 | 24.1 | 8.8 | 1.4 |
| 22 | 19.6 | 40.5 | 21.4 | 1.8 |
| 30 | 28.7 | 18.7 | 20.4 | 1.2 |
| 32 | 20.5 | 40.1 | 16.0 | 1.1 |
| 46 | 2.4 | 0.8 | 0.6 | 0.2 |
| 47 | 2.1 | 3.7 | 3.9 | 0.5 |
| 48 | 9.2 | 14.7 | 11.3 | 1.4 |
| 50 | | | | 15.8 |
| 57 | 9.4 | 33.9 | 21.7 | 6.7 |
| 64 | 58.8 | 135.6 | 186.6 | 7.0 |
| 65 | 39.2 | 105.8 | 115.0 | 9.6 |
| 66 | 20.6 | 17.5 | 16.8 | 1.4 |
| 69 | 7.5 | 11.6 | 7.5 | 1.0 |
| 70 | 26.9 | 30.3 | 30.7 | 3.2 |
| 72 | 21.0 | 93.7 | 78.8 | 2.2 |

The present invention also provides pharmaceutical compositions containing one or more compounds of the invention, for example a compound of formula I or their pharmaceutically acceptable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compounds of the present invention are GABA A α5 receptor inhibitors. The invention also provides a method for enhancing cognition or for treating a disorder selected from the group consisting of cognitive disorders, anxiety, schizophrenia and Alzheimer's disease which comprises administering to an individual a therapeutically effective amount of a compound of formula I or a pharmaceutically acceptable salt thereof. In particular, the invention provides a method for treating Alzheimer's disease which comprises administering to an individual a therapeutically effective amount of a compound of formula I or a pharmaceutically acceptable salt thereof.

The compounds and compositions of the present invention can be administered in a conventional manner, for example, orally, rectally, or parenterally. The compounds of the invention can be administered orally, for example, in the form of tablets, coated tablets, dragèes, hard and soft gelatine capsules, solutions, emulsions, or suspensions. The compounds of the invention can be administered rectally, for example, in the form of suppositories or parenterally, for example, in the form of injectable solutions.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C.

Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples are provided for illustration of the invention. They should not be considered as limiting the scope of the invention, but merely as being representative thereof.

EXAMPLE 1

10-Chloro-9H-imidazo[1,5-a][1,2,4]triazolo[1,5-d][1,4]benzodiazepine a) 9H-imidazor[1,5-a][1,2,4]triazolo[1,5-d][1,4]benzodiazepine 9H-Imidazo[1,5-a][1,2,4]triazolo[1,5-d][1,4]benzodiazepine-10-carboxylic acid[1] (1.5 g, 5.61 mmol) was heated under argon to 290° C. to 310° C. for 10 min ($CO_2$-evolution). The residue was purified by chromatography ($SiO_2$, chloroform:ethanol=100:0 to 98:2) and recrystallised from ethyl acetate affording the title compound (1.05 g, 84%) as an off-white crystalline solid. MS: m/e 224.2 $[M+H]^+$.

b) 10-Chloro-9H-imidazo[1,5-a][1,2,4]triazolo[1,5-d][1,4]benzodiazepine

To a solution of 9H-imidazo[1,5-a][1,2,4]triazolo[1,5-d][1,4]benzodiazepine (100 mg, 0.45 mmol) in DMF (2.3 mL) was added N-chlorosuccinimide at ambient temperature. The resulting mixture was stirred for 90 h at this temperature and was then extracted with dichloromethane (2×20 mL). The combined organic layers were washed with water (20 mL) and dried over sodium sulfate. Purification by chromatography ($SiO_2$, heptane:ethyl acetate:dichloromethane=75:15:10) and trituration in water (20 mL) afforded the title compound (37 mg, 32%) as a white solid. MS: m/e=258.0 $[M+H]^+$.

EXAMPLE 2

10-Chloro-3-fluoro-9H-imidazo[1,5-a][1,2,4]triazolo[1,5-d][1,4]benzodiazepine a) 3-Fluoro-9H-imidazo[1,5-a][1,2,4]triazolo[1,5-d][1,4]benzodiazepine A suspension of 3-fluoro-9H-imidazo[1,5-a][1,2,4]triazolo[1,5-d][1,4]benzodiazepine-10-carboxylic acid[1] (25.3 g, 88.5 mmol) in diethylene glycol dibutyl ether (100 mL) was stirred for 48 h at 200° C. under a nitrogen-atmosphere. The resulting suspension was treated with 500 mL heptane, stirred for 0.5 h at 0° C. Filtration and washing with heptane (2×100 mL) afforded the title compound (20.5 g, 96%) as an off-white solid. MS: m/e=242.3 $[M+H]^+$.

b) 10-Chloro-3-fluoro-9H-imidazo[1,5-a][1,2,4]triazolo[1,5-d][1,4]benzodiazepine To a suspension of 3-fluoro-9H-imidazo[1,5-a][1,2,4]triazolo[1,5-d][1,4]benzodiazepine (5.66 g, 2.35 mmol) in DMF (56 mL) was added 1,3-dichloro-5,5-dimethylhydantoin (2.54 g, 1.29 mmol) in portions over a period of 5 h at ambient temperature. The mixture was stirred for further 18 h at this temperature and was diluted with ethyl acetate (150 mL), washed with aqueous sodium carbonate (100 mL) and extracted with ethyl acetate (150 mL). Drying over sodium sulfate and purification by chromatography ($SiO_2$, dichloromethane:ethyl acetate=7:3 to 5:5) afforded the title compound (4.24 g, 66%) as a white solid. MS: m/e=276.0 [M+H]$^+$.

EXAMPLE 3

10-Chloro-3-methoxy-9H-imidazo[1,5-a][1,2,4]triazolo[1,5-d][1,4]benzodiazepine a) 3-Methoxy-9H-imidazo[1,5-a][1,2,4]triazolo[1,5-d][1,4]benzodiazepine To a suspension of 3-fluoro-9H-imidazo[1,5-a][1,2,4]triazolo[1,5-d][1,4]benzodiazepine (1.00 g, 4.15 mmol) in DMSO (10 mL) was added sodium methoxide (291 mg, 5.39 mmol). The mixture was stirred for 3 h at 150° C. After addition of another sodium methoxide (291 mg, 5.39 mmol) stirring at 150° C. was continued for further 3 h. The mixture was concentrated in vacuo and the residue purified by chromatography (SiO$_2$, ethyl acetate: methanol=100:0 to 90:10) affording the title compound (650 mg, 62%) as a white solid. MS: m/e=254.1 [M+H]$^+$.

b) 10-Chloro-3-methoxy-9H-imidazo[1,5-a][1,2,4]triazolo[1,5-d][1,4]benzodiazepine To a solution of 3-methoxy-9H-imidazo[1,5-a][1,2,4]triazolo[1,5-d][1,4]benzodiazepine (200 mg, 0.79 mmol) in DMF (3 mL) was added N-chlorosuccinimide (116 mg, 0.87 mmol) and the resulting suspension was stirred for 14 d at ambient temperature. The mixture was diluted with ethyl acetate (20 mL) and washed with aqueous sodium carbonate (2 N). After extraction with ethyl acetate (20 mL), the combined layers were washed with water (20 mL) and dried over sodium sulfate. Purification by chromatography (SiO$_2$, heptane:ethyl acetate:dichloromethane=7:2:1 to 4:5:1) afforded the title compound (47 mg, 21%) as awhite solid. MS: m/e=288.0 [M+H]$^+$.

EXAMPLE 4

10-Chloro-3-ethoxy-9H-imidazo[1,5-a][1,2,4]triazolo[1,5-d][1,4]benzodiazepine a) 3-Ethoxy-9H-imidazo[1,5-a][1,2,4]triazolo[1,5-d][1,4]benzodiazepine To a solution of 3-fluoro-9H-imidazo[1,5-a][1,2,4]triazolo[1,5-d][1,4]benzodiazepine (600 mg, 2.49 mmol) in DMSO (6 mL) was added a solution of sodium ethoxide in ethanol (21%, 1.20 mL, 3.23 mmol) and stirred for 4 h at 130° C. The mixture was concentrated in vacuo and the residue purified by chromatography (SiO$_2$, ethyl acetate:dichloromethane: methanol=8:2:0 to 6:2:2) affording the title compound (613 mg, 92%) as a white solid. MS: m/e=268.2 [M+H]$^+$.

b) 10-Chloro-3-ethoxy-9H-imidazo[1,5-a][1,2,4]triazolo[1,5-d][1,4]benzodiazepine To a solution of 3-ethoxy-9H-imidazo[1,5-a][1,2,4]triazolo[1,5-d][1,4]benzodiazepine (200 mg, 0.75 mmol) in DMF (2 mL) was added at ambient temperature 1,3-dichloro-5,5-dimethylhydantoin (81 mg, 0.41 mmol) and stirred for 24 h. Another portion of 1,3-dichloro-5,5-dimethylhydantoin (40 mg, 0.15 mmol) was added and stirring was continued for further 18 h at ambient tempreature. The mixture was diluted with ethyl acetate (20 mL), washed with aqueous sodium carbonate and dried over sodium sulfate. Purification by chromatography (SiO$_2$, heptane:ethyl acetate:dichloromethane=6:2:2 to 3:5:2) afforded the title compound (126 mg, 56%) as a white solid. MS: m/e=302.0 [M+H]$^+$.

EXAMPLE 5

3-Benzyloxy-10-chloro-9H-imidazo[1,5-a][1,2,4]triazolo[1,5-d][1,4]benzodiazepine a) 3-Benzyloxy-9H-imidazo[1,5-a][1,2,4]triazolo[1,5-d][1,4]benzodiazepine To a solution of benzyl alcohol (1.1 mL, 10 mmol) in DMSO (5 mL) was added at ambient temperature sodium hydride (55% dispersion in mineral oil, 136 mg, 3.11 mmol) and stirred for 2 h. 3-Fluoro-9H-imidazo[1,5-a][1,2,4]triazolo[1,5-d][1,4]benzodiazepine 2.07 mmol) was added and stirred for 3 h at 130° C. Water (15 mL) was added slowly and the resulting suspension was stirred for 15 min at ambient temperature. Filtration, washing with water (3 mL) and purification by chromatography (SiO$_2$, ethyl acetate:dichloromethane:methanol=8:2:0) afforded the title compound (490 mg, 72%) as a white solid. MS: m/e=330.1 [M+H]$^+$.

b) 3-Benzyloxy-10-chloro-9H-imidazo[1,5-a][1,2,4]triazolo[1,5-d][1,4]benzodiazepine As described for example 4b), 3-benzyloxy-9H-imidazo[1,5-a][1,2,4]triazolo[1,5-d][1,4]benzo-diazepine (410 mg, 1.25 mmol), instead of 3-ethoxy-9H-imidazo[1,5-a][1,2,4]-triazolo[1,5-d][1,4]benzodiazepine, was converted to the title compound (SiO$_2$, heptane:ethyl acetate:dichloromethane=6:2:2 to 3:5:2, 276 mg, 61%) which was obtained as a white foam. MS: m/e=364.1 [M+H]$^+$.

EXAMPLE 6

10-Chloro-3-phenoxy-9H-imidazo[1,5-a][1,2,4]triazolo[1,5-d][1,4]benzodiazepine a) 3-Phenoxy-9H-imidazo[1,5-a][1,2,4]triazolo[1,5-d][1,4]benzodiazepine As described for example 5a), 3-fluoro-9H-imidazo[1,5-a][1,2,4]triazolo[1,5-d][1,4]benzo-diazepine (500 mg, 2.07 mmol) was converted using phenol instead of benzylalcohol to the title compound (SiO$_2$, ethyl acetate:dichloromethane:methanol=8:2:0 to 6:2:2, 330 mg, 51%) which was obtained as a white solid. MS: m/e=316.0 [M+H]$^+$.

b) 10-Chloro-3-phenoxy-9H-imidazo[1,5-a][1,2,4]triazolo[1,5-d][1,4]benzodiazepine As described for example 4b), 3-phenoxy-9H-imidazo[1,5-a][1,2,4]triazolo[1,5-d][1,4]benzo-diazepine (410 mg, 1.25 mmol), instead of 3-ethoxy-9H-imidazo[1,5-a][1,2,4]triazolo[1,5-d][1,4]benzodiazepine, was converted to the title compound (SiO$_2$, heptane:ethyl acetate:dichloromethane=7:2:1 to 4:5:1, 183 mg, 72%) which was obtained as a white solid. MS: m/e=350.2 [M+H]$^+$.

EXAMPLE 7

10-Chloro-3-(2-fluoro-ethoxy)-9H-imidazo[1,5-a][1,2,4]triazolo[1,5-d][1,4]benzodiazepine Sodium hydride (55% dispersion in mineral oil, 158 mg, 3.6 mmol) was added to DMSO (5 mL) and stirred for 15 min at ambient temperature. 2-Fluoroethanol (524 μl, 9.1 mmol) was added dropwise and stirring was continued for further 1.5 h. After addition of 10-chloro-3-fluoro-9H-imidazo[1,5-a][1,2,4]triazolo[1,5-d][1,4]benzodiazepine (200 mg, 0.73 mmol) the reaction mixture was heated to 130° C. for 3 h before it was diluted with ethyl acetate (20 mL), washed with aqueous Na$_2$CO$_3$ and extracted with ethyl acetate (20 mL). Drying

17 over sodium sulfate and purification by chromatography (SiO$_2$, heptane:ethyl acetate:dichloromethane=6:2:2 to 3:5:2) afforded the title compound (107 mg, 46%) as a white solid. MS: m/e=320.2 [M+H]$^+$.

EXAMPLE 8

10-Chloro-3-(2,2-difluoro-ethoxy)-9H-imidazo[1,5-a][1,2,4]triazolo[1,5-d][1,4]benzodiazepine As described for example 7, 10-chloro-3-fluoro-9H-imidazo[1,5-a][1,2,4]triazolo[1,5-d][1,4]-benzodiazepine (400 mg, 1.45 mmol) was converted using 2,2-difluoroethanol instead of 2-fluoroethanol to the title compound (SiO$_2$, heptane:ethyl acetate:dichloromethane=6:2:2 to 3:5:2, 243 mg, 50%) which was obtained as a white solid. MS: m/e=338.1 [M+H]$^+$.

EXAMPLE 9

10-Chloro-3-(2,2,2-trifluoro-ethoxy)-9H-imidazo[1,5-a][1,2,4]triazolo[1,5-d][1,4]benzodiazepine As described for example 7, 10-chloro-3-fluoro-9H-imidazo[1,5-a][1,2,4]triazolo[1,5-d][1,4]benzodiazepine (200 mg, 0.73 mmol) was converted using 2,2,2-trifluoroethanol instead of 2-fluoroethanol to the title compound (SiO$_2$, heptane:ethyl acetate:dichloromethane=6:2:2 to 3:5:2, 62 mg, 24%) which was obtained as awhite solid. MS: m/e=356.1 [M+H]$^+$.

EXAMPLE 10

10-Chloro-3-vinyloxy-9H-imidazo[1,5-a][1,2,4]triazolo[1,5-d][1,4]benzodiazepine

Sodium hydride (55% dispersion in mineral oil, 158 mg, 3.6 mmol) was added to DMSO (5 mL) and stirred for 15 min at ambient temperature. 2-Fluoroethanol (524 µl, 9.1 mmol) was added dropwise and stirring was continued for further 1.5 h. After addition of 10-chloro-3-fluoro-9H-imidazo[1,5-a][1,2,4]triazolo[1,5-d][1,4]benzodiazepine (200 mg, 0.73 mmol) the reaction mixture was heated to 130° C. for 3 h before it was diluted with ethyl acetate (20 mL), washed with aqueous Na$_2$CO$_3$ and extracted with ethyl acetate (20 mL). Drying over sodium sulfate and purification by chromatography (SiO$_2$, heptane:ethyl acetate:dichloromethane=6:2:2 to 3:5:2) afforded the title compound (32 mg, 15%) as a white solid. MS: m/e=300.2 [M+H]$^+$.

EXAMPLE 11

10-Chloro-3-(2-hydroxy-ethoxy)-9H-imidazo[1,5-a][1,2,4]triazolo[1,5-d][1,4]benzodiazepine To a suspension of 10-chloro-3-fluoro-9H-imidazo[1,5-a][1,2,4]triazolo[1,5-d][1,4]benzo-diazepine (200 mg, 0.73 mmol) in ethylene glycol (2 mL) was added potassium hydroxide (81 mg, 1.5 mmol) and the reaction mixture was stirred for 2 h at 170° C. The resulting solution was diluted with ethyl acetate (20 mL), washed aqueous Na$_2$CO$_3$ and extracted with ethyl acetate (20 mL). Drying over sodium sulfate and purification by chromatography (SiO$_2$, ethyl acetate:methanol=1:0 to 9:1) afforded the title compound (79 mg, 34%) as a white solid. MS: m/e=318.1 [M+H]$^+$.

18

EXAMPLE 12

10-Chloro-3-methylamino-9H-imidazo[1,5-a][1,2,4]triazolo[1,5-d][1,4]benzodiazepine To a solution of 3-acetylamino-10-chloro-9H-imidazo[1,5-a][1,2,4]triazolo[1,5-d][1,4]benzo-diazepine (840 mg, 2.67 mmol) in DMF (16 mL) was added potassium bis(trimethylsilyl)amide (0.9 M in THF, 3.81 mL, 3.47 mmol) and the mixture was stirred for 45 min at ambient temperature. Methyliodide (217 mL, 3.47 mmol) was added and stirring was continued for further 2 h. The reaction mixture was diluted with ethyl acetate and aqueous Na$_2$CO$_3$ and extracted with ethyl acetate. The combined organic layers were washed with brine and dried over sodium sulfate. Purification by chromatography (SiO$_2$, heptan:ethyl acetate:dichloromethane=6:2:2 to 3:5:2) afforded the title compound (65 mg, 9%) as a white cristalline solid. MS: m/e=287.1 [M+H]$^+$.

EXAMPLE 13

10-Chloro-3-dimethylamino-9H-imidazo[1,5-a][1,2,4]triazolo[1,5-d][1,4]benzodiazepine To a solution of dimethylamine hydrochloride (621 mg, 7.62 mmol) in DMSO (3 mL) was added sodium hydride (55% dispersion in mineral oil, 261 mg, 10.9 mmol) and the mixture was stirred for 1.5 h at ambient temperature. 10-Chloro-3-fluoro-9H-imidazo[1,5-a][1,2,4]triazolo[1,5-d][1,4]benzodiazepine (300 mg, 1.09 mmol) was added and stirred for 2 d at 130° C. The reaction mixture was diluted with water (30 mL) and extracted with ethyl acetate (30 mL). The organic layers were washed with water (30 mL) and brine (20 mL). Drying over sodium sulfate and purification by chromatography (SiO$_2$, heptane:ethyl acetate:dichloromethane=6:2:2 to 3:5:2) afforded the title compound (94 mg, 29%) as a white solid. MS: m/e=301.2 [M+H]$^+$.

EXAMPLE 14

3-Benzylamino-10-chloro-9H-imidazo[1,5-a][1,2,4]triazolo[1,5-d][1,4]benzodiazepine A mixture of 10-chloro-3-fluoro-9H-imidazo[1,5-a][1,2,4]triazolo[1,5-d][1,4]benzodiazepine (400 mg, 1.45 mmol) and benzylamine (793 µL, 7.26 mmol) was stirred for 4 d at 130° C., before water (10 mL) was added. It was extracted with ethyl acetate (20 mL) and washed subsequently with aqueous Na$_2$CO$_3$ (20 mL) and water (20 mL). Drying over sodium sulfate and purification by chromatography (SiO$_2$, heptane:ethyl acetate:dichloromethane=7:2:1 to 4:5: 1) afforded the tide compound (120 mg, 23%) as a yellow solid. MS: m/e=363.1 [M+H]$^+$.

EXAMPLE 15

3-(Benzyl-methyl-amino)-10-chloro-9H-imidazo[1,5-a][1,2,4]triazolo[1,5-d][1,4]benzodiazepine To a solution of 3-benzylamino-10-chloro-9H-imidazo[1,5-a][1,2,4]triazolo[1,5-d][1,4]benzo-diazepine (104 mg, 0.29 mmol) in DMF (1 mL) was added potassium, bis(trimethylsilyl)amide (0.9 M in THF, 410 µL, 0.37 mmol) and the mixture was stirred for 45 min at ambient temperature. After addition of methyl iodide (23 µL, 0.37 mmol) stirring was continued for further 20 h. The reaction mixture was diluted with ethyl acetate (30 mL) and aqueous Na$_2$CO$_3$. The aqueous layer was extracted with ethyl acetate (30 mL) and the combined organic layers were dried over sodium sulfate. Purification by chromatography (SiO$_2$, heptane:ethyl acetate:

dichloromethane=7:2:1 to 4:5:1) afforded the title compound (26 mg, 24%) as a light brown solid. MS: m/e=377.0 [M+H]⁺.

EXAMPLE 16

10-Chloro-3-morpholin-4-yl-9H-imidazo[1,5-a][1,2,4]triazolo[1,5-d][1,4]benzodiazepine To a solution of 10-chloro-3-fluoro-9H-imidazo[1,5-a][1,2,4]triazolo[1,5-d][1,4]benzodiazepine (206 mg, 0.75 mmol) in DMSO (2 mL) in a sealed tube was added morpholine (98 µl, 1.1 mmol) and the mixture was stirred for 18 h at 130° C. Further morpholine (325 µl, 3.74 mmol) was added and stirring was continued for another 48 h at 130° C. The reaction mixture was diluted with ethyl acetate (20 mL), washed aqueous $Na_2CO_3$ and extracted with ethyl acetate (20 mL). Drying over sodium sulfate and purification by chromatography ($SiO_2$, heptane:ethyl acetate:dichloromethane:methanol=5:3:2:0 to 0:75:20:5) afforded the title compound (182 mg, 71%) as a white solid. MS: m/e=343.1 [M+H]⁺.

EXAMPLE 17

10-Chloro-3-thiomorpholin-4-yl-9H-imidazo[1,5-a][1,2,4]triazolo[1,5-d][1,4]benzodiazepine To a solution of 10-chloro-3-fluoro-9H-imidazo[1,5-a][1,2,4]triazolo[1,5-d][1,4]benzodiazepine (500 mg, 1.81 mmol) in DMSO (5 mL) was added thiomorpholine (935 mg, 9.1 mmol) and the mixture was stirred for 18 h at 130° C. and 3 d at 150° C. The reaction mixture was diluted with ethyl acetate (20 mL), washed aqueous $Na_2CO_3$ and extracted with ethyl acetate (20 mL). Drying over sodium sulfate and purification by chromatography ($SiO_2$, heptane:ethyl acetate:dichloromethane=6:2:2 to 3:5:2) afforded the title compound (490 mg, 75%) as a light brown solid. MS: m/e=359.2 [M+H]⁺.

EXAMPLE 18

10-Chloro-3-imidazol-1-yl-9H-imidazo[1,5-a][1,2,4]triazolo[1,5-d][1,4]benzodiazepine Sodium hydride (55% dispersion in mineral oil, 126 mg, 2.90 mmol) was added to DMSO (4 mL) and stirred for 15 min at ambient temperature. Imidazole (493 mg, 7.26 mmol) was added at ambient temperature and stirred was continued for further 18 h. After addition of 10-chloro-3-fluoro-9H-imidazo[1,5-a][1,2,4]triazolo[1,5-d][1,4]benzodiazepine (400 mg, 1.45 mmol) the mixture was heated for 3 h to 80° C. The reaction mixture was diluted with ethyl acetate (20 mL), washed aqueous $Na_2CO_3$ and extracted with ethyl acetate (20 mL). Drying over sodium sulfate and purification by chromatography ($SiO_2$, ethyl acetate:methanol=9:1) afforded the title compound (82 mg, 17%) as a white solid. MS: m/e=324.1 [M+H]⁺.

EXAMPLE 19

3-Acetyl-amino-10-chloro-9H-imidazo[1,5-a][1,2,4]triazolo[1,5-d][1,4]benzodiazepine a) 3-Amino-9H-imidazo[1,5-a][1,2,4]triazolo[1,5-d][1,4]benzodiazepine A mixture of 3-fluoro-9H-imidazo[1,5-a][1,2,4]triazolo[1,5-d][1,4]benzodiazepine (5.00 g, 20.7 mmol) and benzylamine (50.0 mL, 458 mmol) was heated for 22 h to 190° C. After evaporation the residue was dissolved in ethyl acetate and washed with water and brine. The aqueous layers were extracted with ethyl acetate. Drying over sodium sulfate afforded crude material of 3-benzylamino-9H-imidazo[1,5-a][1,2,4]triazolo[1,5-d][1,4]benzodiazepine as a brown solid which was dissolved in methanol (100 mL). After addition of palladium (10% on activated carbon, 680 mg, 0.64 mmol) the mixture was stirred under a hydrogen atmosphere for 2 h at 70° C. Aqueous HCl (1N, 32 mL) was added and the reaction mixture was stirred under a hydrogen atmosphere for 19 h at 90° C. Filtration over Hyflo® was followed by addition of dichloromethane and aqueous $Na_2CO_3$ and the aqueous layers were extracted with dichloromethane. Drying over sodium sulfate and purification by chromatography ($SiO_2$, ethyl acetate:dichloromethane:methanol=9:2:0 to 6:2:2) afforded the title compound (2.36 g, 48%) as a light brown solid. MS: m/e=239.1 [M+H]⁺.

b) 3-Acetylamino-9H-imidazo[1,5-a][1,2,4]triazolo[1,5-d][1,4]benzodiazepine

To a solution of 3-amino-9H-imidazo[1,5-a][1,2,4]triazolo[1,5-d][1,4]benzodiazepine (2.63 g, 9.91 mmol) in dichloromethane (100 mL) were added pyridine (1.78 mL, 22.1 mmol) and acetic anhydride (1.25 mL, 13.2 mmol). The resulting suspension was stirred for 18 h at ambient temperature. After addition of aqueous $Na_2CO_3$ the resulting cristalline solid was filtered and washed with aqueous $Na_2CO_3$ and water. Drying in vacuo afforded the title compound (1.22 g, 44%) as an off-white solid. MS: m/e=281.1 [M+H]⁺.

c) 3-Acetylamino-10-chloro-9H-imidazo[1,5-a][1,2,4]triazolo[1,5-d][1,4]benzodiazepine As described for example 4b), 3-acetylamino-9H-imidazo[1,5-a][1,2,4]triazolo[1,5-d][1,4]benzo-diazepine (1.20 mg, 4.28 mmol), instead of 3-ethoxy-9H-imidazo[1,5-a][1,2,4]triazolo[1,5-d][1,4]benzodiazepine, was converted to the title compound ($SiO_2$, dichloromethane:methanol=97:3 to 95:5, 840 mg, 62%) which was obtained as a white solid. MS: m/e=315.1 [M+H]⁺.

EXAMPLE 20

3,10-Dichloro-9H-imidazo[1,5-a][1,2,4]triazolo[1,5-d][1,4]benzodiazepine a) 3-Chloro-9H-imidazo[1,5-a][1,2,4]triazolo[1,5-d][1,4]benzodiazepine As described for example 2a), 3-chloro-9H-imidazo[1,5-a][1,2,4]triazolo[1,5-d][1,4]benzo-diazepine-10-carboxylic acid (EP 519 307) (17.5 g, 57.8 mmol), instead of 3-fluoro-9H-imidazo[1,5-a][1,2,4]-triazolo[1,5-d][1,4]benzodiazepine-10-carboxylic acid, was converted to the title compound (14.1 g, 94%) which was obtained as an off-white solid. MS: m/e=258.0 [M+H]⁺.

b) 3,10-Dichloro-9H-imidazo[1,5-a][1,2,4]triazolo[1,5-d][1,4]benzodiazepine

As described for example 1b), 3-chloro-9H-imidazo[1,5-a][1,2,4]triazolo[1,5-d][1,4]benzo-diazepine (302 mg, 1.17 mmol), instead of 3-fluoro-9H-imidazo[1,5-a][1,2,4]triazolo[1,5-d][1,4]-benzodiazepine, was converted to the title compound (ethyl acetate:heptane:dichloromethane=4:5:1 to 8:1:1, 236 mg, 69%) which was obtained as a white solid. MS: m/e=292.0 [M]⁺.

EXAMPLE 21

3-Bromo-10-chloro-9H-imidazo[1,5-a][1,2,4]triazolo[1,5-d][1,4]benzodiazepine a) (4-Bromo-2-cyano-phenyl)-carbamic acid ethyl ester A suspension of 2-amino-5-bromobenzonitrile (58.5 g, 297 mmol) in ethyl chloroformate (141 mL, 1.48 mol) was heated at reflux for 5 h. The excess ethyl chloroformate (99 mL) was distilled off and toluene (96 mL) was added. Slow addition of cyclohexane (228 mL) induced crystallization. The resulting solid was collected by filtration and rinsed with cyclohexane. Drying in vacuo afforded the title compound (54.3 g, 68%) as an orange solid. MS: m/e=267.1/269.2 [M—H⁻].

b) 9-Bromo-6H-[1,2,4]triazolo[1,5-c]quinazolin-5-one

To a solution of (4-bromo-2-cyano-phenyl)-carbamic acid ethyl ester (40.4 g, 150 mmol) in NMP (170 mL) was added formylhydrazine (10.0 g, 150 mmol). The resulting mixture was stirred for 1.5 h at 160° C. under a gentle nitrogen sweep. It was cooled to below 100° C. and water (340 mL) was added slowly. The resulting slurry was cooled to 25° C. and stirred for 15 min. The solid was collected by filtration and washed with water and 2-propanol. Drying in vacuo afforded the title compound (32.4 g, 81%) as a light yellow solid. MS: m/e 264.9/267.0 [M+H⁺].

c) 4-Bromo-2-(2H-[1,2,4]triazol-3-yl)-phenylamine

To a well stirred slurry of 9-bromo-6H-[1,2,4]triazolo[1,5-c]quinazolin-5-one (32.0 g, 171 mmol) in ethylene glycol (146 mL) which was heated at 100° C., was added aqeous NaOH (32%, 22.4 mL, 241 mmol). The slurry was heated at 140° C. for 17.5 h. The resulting solution was cooled to 27° C. and the product began to crystallize. Water (146 mL) and 1-octanol (1.73 mL) were added and the pH of the suspension was adjusted to 6.5 by the slow addition of glacial acetic acid (14 mL). The resulting slurry was stirred for 30 min, the solid was collected by filtration and washed with water and 2-propanol. Drying in vacuo afforded the title compound (25.2 g, 87%) as a light yellow solid. MS: m/e=239.0/241.1 [M+H⁺].

d) 9-Bromo-6H-1,3,3a,6-tetraaza-benzo[e]azulen-5-one

A solution of 4-bromo-2-(2H-[1,2,4]triazol-3-yl)-phenylamine (25.0 g, 105 mmol) in dioxane (870 mL) and pyridine (10.0 mL) was cooled to 12° C. A solution of chloroacetyl chloride (9.56 mL, 121 mmol) in diethylether (34.7 mL) was added dropwise over a period of 8 min. The mixture was stirred at 10-12° C. for 75 min and treated within 5 min with aq NaOH (2 N, 126 mL, 251 mmol). The mixture was stirred for 17.5 h at ambient temperature. The pH thereby dropped to about pH=9 and it was adjusted to pH=8 with HCl (3 N, 6 mL). After evaporation the residue was stirred at 15° C. for 30 min in water (650 mL) and ethyl acetate (22 mL). The crystals were filtered off, washed with cold water and dried in vacuo. Trituration in ethyl acetate (100 mL) afforded the title compound (13.4 g, 46%) as a light yellow solid. MS: m/e =279.0/281.0 [M+H⁺].

e) Ethyl 3-bromo-9H-imidazo[1,5-a][1,2,4]triazolo[1,5-d][1,4]benzodiazepine-10-carboxylate To a suspension of 9-bromo-6H-1,3,3a,6-tetraaza-benzo[e]azulen-5-one (10.7 g, 38.5 mmol) in chloroform (270 mL, filtrated over Alox basic) was added 4,N,N-trimethylaniline (13.9 mL, 96.1 mmol) and phosphorous oxychloride (5.28 mL, 57.7 mmol). The mixture was stirred for 22 h at reflux, then cooled to 30° C. and poured into aq NaHCO₃ (10%, 575 mL). After extraction with chloroform (50 mL) the organic layers were dried over sodium sulfate and concentrated. In the meantime potassium tert-butylate (4.31 g, 38.5 mmol) was added in portions to a solution of ethyl isocyanoacetate (4.42 mL, 38.5 mmol) in THF (115 mL) at −25° C. to −10° C. The resulting suspension was stirred for 45 min at −10° C. and then cooled to −65° C. The solution from above was added dropwise within 10 min and the mixture was stirred for 16 h at ambient temperature. Acetic acid (1.6 mL) was added, stirred for 15 min and then poured into aq NaHCO₃ (5%, 460 mL) and ethyl acetate (96 mL). The resulting crystals were filtered off, washed with ethyl acetate (25 mL), water (50 mL) and ethyl acetate (25 mL). Drying in vacuo afforded the title compound (4.81 g, 33%) as a light brown solid. MS: m/e=373.7/375.7 [M]⁺.

f) 3-Bromo-9H-imidazo[1,5-a][1,2,4]triazolo[1,5-d][1,4]benzodiazepine-10-carboxylic acid A mixture of ethyl 3-bromo-9H-imidazo[1,5-a][1,2,4]triazolo[1,5-d][1,4]benzodiazepine-10-carboxylate (7.08 g, 18.9 mmol), NaOH 1N (76 mL, 76 mmol) in ethanol (70 mL) was stirred for 18 h at ambient temperature. The solvent was distilled off (55 mbar, 45° C.) and the resulting light brown suspension was adjusted with aqueous HCl (1 N, 85 mL) to pH=1.5 at 0° C. The suspension was stirred for 1 h at 0° C., filtered off and washed twice with water (total 50 mL). The solid was dried in vacuo at 60° C. affording the title compound (6.65 g, 99%) as a light brown solid. MS: m/e=346.0/348.2 [M+H⁺].

g) 3-Bromo-9H-imidazo[1,5-a][1,2,4]triazolo[1,5-d][1,4]benzodiazepine

As described for example 2a), 3-bromo-9H-imidazo[1,5-a][1,2,4]triazolo[1,5-d][1,4]benzo-diazepine-10-carboxylic acid (6.25 g, 18.1 mmol), instead of 3-fluoro-9H-imidazo[1,5-a][1,2,4]triazolo[1,5-d][1,4]benzodiazepine-10-carboxylic acid, was converted to the title compound (SiO₂, ethyl acetate:dichloromethane:methanol=75:20:5, 4.20 g, 77%) which was obtained as an off-white solid. MS: m/e=301.9/304.0 [M+H]⁺.

h) 3-Bromo-10-chloro-9H-imidazo[1,5-a][1,2,4]triazolo[1,5-d][1,4]benzodiazepine

As described for example 2b), 3-bromo-9H-imidazo[1,5-a][1,2,4]triazolo[1,5-d][1,4]benzo-diazepine (4.00 g, 13.2 mmol), instead of 3-fluoro-9H-imidazo[1,5-a][1,2,4]triazolo[1,5-d][1,4]-benzodiazepine, was converted to the title compound (SiO₂, heptane:ethyl acetate:dichloromethane=6:2:2 to 2:4:4, 2.69 g, 60%) which was obtained as a white solid. MS: m/e=335.9/337.9 [M+H]⁺.

EXAMPLE 22

10-Chloro-3-methyl-9H-imidazo[1,5-a][1,2,4]triazolo[1,5-d][1,4]benzodiazepine a) 3-Methyl-9H-imidazo[1,5-a][1,2,4]triazolo[1,5-d][1,4]benzodiazepine As-described for example 2a), 3-methyl-9H-imidazo[1,5-a][1,2,4]triazolo[1,5-d][1,4]benzo-diazepine-10-carboxylic acid (EP 519 307) (400 mg, 1.42 mmol), instead of 3-fluoro-9H-imidazo[1,5-a][1,2,4]triazolo[1,5-d][1,4]benzodiazepine-10-carboxylic acid, was converted to the title compound (SiO₂, ethyl acetate:dichloromethane:methanol=8:2:0 to 7:2:1, 240 mg, 71%) which was obtained as a white solid. MS: m/e=238.1 [M+H]⁺.

b) 10-Chloro-3-methyl-9H-imidazo[1,5-a][1,2,4]triazolo[1,5-d][1,4]benzodiazepine As described for example 2b), 3-methyl-9H-imidazo[1,5-a][1,2,4]triazolo[1,5-d][1,4]benzo-diazepine (210 mg, 0.89 mmol), instead of 3-fluoro-9H-imidazo[1,5-a][1,2,4]triazolo[1,5-d][1,4]-benzodiazepine, was converted to the title compound (SiO$_2$, heptane:ethyl acetate:dichloromethane=7:2:1 to 4:5:1, 120 mg, 50%) which was obtained as a white solid. MS: m/e=272.0 [M+H]$^+$.

EXAMPLE 23

10-Chloro-3-trimethylsilanylethynyl-9H-imidazo[1,5-a][1,2,4]triazolo[1,5-d][1,4]benzodiazepine A suspension of 3-bromo-10-chloro-9H-imidazo[1,5-a][1,2,4]triazolo[1,5-d][1,4]benzodiazepine (800 mg, 2.38 mmol), trimethylsilylacetylene (0.51 mL, 3.68 mmol), bis(triphenylphosphine)-palladium(II) chloride (83 mg, 0.12 mmol), triphenylphosphine (19 mg, 0.07 mmol) and triethylamine (1.2 mL, 8.6 mmol) in THF (12 mL) was stirred for 15 min at ambient temperature. Copper(I) bromide (3 mg, 0.02 mmol) was added and the reaction mixture was stirred for 18 h at 70° C. under an argon atmosphere. The mixture was diluted with ethyl acetate (50 mL) and washed with aqueous citric acid (10%, 100 mL). The aqueous phase was extracted with ethyl acetate (100 mL) and the combined organic layers were dried over sodium sulfate. Purification by chromatography (SiO$_2$, heptane:ethyl acetate:dichloromethane:methanol=7:2:1:0 to 0:7:1:2) afforded the title compound (820 mg, 97%) as a white solid. MS: m/e=354.2 [M+H]$^+$.

EXAMPLE 24

10-Chloro-3-ethynyl-9H-imidazo[1,5-a][1,2,4]triazolo[1,5-d][1,4]benzodiazepine

To a solution of 10-chloro-3-trimethylsilanylethynyl-9H-imidazo[1,5-a][1,2,4]triazolo[1,5-d][1,4]benzodiazepine (750 mg, 2.12 mmol) in a mixture of THF (7.5 mL) and MeOH (0.4 mL) was added under an argon atmosphere at −70° C. tetrabutylammonium fluoride trihydrate (702 mg, 2.23 mmol). The dry ice bath was replaced with an ice bath and the reaction mixture was stirred for 1 h at 0° C. It was diluted with ethyl acetate (20 mL), washed with aqueous Na$_2$CO$_3$ and extracted with ethyl acetate (20 mL). Drying over sodium sulfate and purification by chromatography (SiO$_2$, heptane:ethyl acetate:dichloromethane=5:5:2) afforded the title compound (443 mg, 74%) as a white solid. MS: m/e=282.0 [M+H]$^+$.

EXAMPLE 25

10-Chloro-3-prop-1-ynyl-9H-imidazo[1,5-a][1,2,4]triazolo[1,5-d][1,4]benzodiazepine A solution of 10-chloro-3-ethynyl-9H-imidazo[1,5-a][1,2,4]triazolo[1,5-d][1,4]benzodiazepine (200 mg, 0.710 mmol) in THF (10 mL) was cooled to −78° C. and butyllithium (1.6 M in hexane, 0.47 mL, 0.75 mmol) was added dropwise. The resulting brown solution was stirred for 45 min at −78° C. before methyl iodide (48 µl, 0.78 mmol) was added at this temperature. The dry ice bath was removed and the reaction mixture was stirred for 18 h at ambient temperature. The reaction mixture was diluted with ethyl acetate (10 mL) and tertbutylmethylether (10 mL) and washed aqueous sodium hydroxide (1 N) and brine. The aqueous layers were washed with THF/TBME 1:1 (10 mL) and the combined organic layers were dried over sodium sulfate. Purification by chromatography (SiO$_2$, heptane:ethyl acetate:triethylamine=63:32:5) afforded the title compound (86 mg, 41%) as a white solid. MS: m/e=296.3 [M+H]$^+$.

EXAMPLE 26

10-Chloro-3-cyclopropylethynyl-9H-imidazo[1,5-a][1,2,4]triazolo[1,5-d][1,4]benzodiazepine As described for example 23) using cyclopropylacetylene instead of trimethylsilylacetylene, 3-bromo-10-chloro-9H-imidazo[1,5-a][1,2,4]triazolo[1,5-d][1,4]benzodiazepine (200 mg, 0.59 mmol) was converted to the title compound (SiO$_2$, heptane:ethyl acetate:dichloromethane=6:2:2 to 3:5:2, 95 mg, 50%) which was obtained as a light brown solid. MS: m/e=322.2 [M+H]$^+$.

EXAMPLE 27

10-Chloro-3-(3-methyl-but-1-ynyl)-9H-imidazo[1,5-a][1,2,4]triazolo[1,5-d][1,4]benzodiazepine As described for example 23) using 3-methyl-1-butyne instead of trimethylsilylacetylene, 3-bromo-10-chloro-9H-imidazo[1,5-a][1,2,4]triazolo[1,5-d][1,4]benzodiazepine (200 mg, 0.59 mmol) was converted to the title compound (SiO$_2$, heptane:ethyl acetate:dichloromethane=6:2:2 to 3:5:2, 39 mg, 20%) which was obtained as a white solid. MS: m/e=324.2 [M+H]$^+$.

EXAMPLE 28

10-Chloro-3-(3-methoxy-prop-1-ynyl))-9H-imidazo[1,5-a][1,2,4]triazolo[1,5-d][1,4]-benzodiazepine As described for example 23) using 3-methoxy-propyne instead of trimethylsilylacetylene, 3-bromo-10-chloro-9H-imidazo[1,5-a][1,2,4]triazolo[1,5-d][1,4]benzodiazepine (200 mg, 0.59 mmol) was converted to the title compound (SiO$_2$, heptane:ethyl acetate:dichloromethane=6:2:2 to 3:5:2, 44 mg, 23%) which was obtained as a white solid. MS: m/e=325.9 [M]$^+$.

EXAMPLE 29

10-Chloro-3-ethyl-9H-imidazo[1,5-a][1,2,4]triazolo[1,5-d][1,4]benzodiazepine

To a solution of 3-bromo-10-chloro-9H-imidazo[1,5-a][1,2,4]triazolo[1,5-d][1,4]benzodiazepine (200 mg, 0.59 mmol) in THF (4 mL) were added diethylzinc solution (1.0 M in hexane, 2.3 mL, 2.3 mmol) and bis(triphenylphosphine)palladium(II) chloride (20-mg, 29 mmol) and the resulting dark brown suspension was stirred for 20 h at ambient temperature under an argon atmosphere. The reaction mixture was diluted with aqueous NH$_4$Cl (sat., 20 mL) and stirred for 30 min before extracting with ethyl acetate (30 mL). Drying over sodium sulfate and purification by chromatography (SiO$_2$, heptane:ethyl acetate:dichloromethane=6:2:2 to 3:5:2) afforded the title compound (39 mg, 23%) as an off-white solid. MS: m/e=286.1 [M+H]$^+$.

EXAMPLE 30

10-Chloro-3-cyclopropyl-9H-imidazo[1,5-a][1,2,4]triazolo[1,5-d][1,4]benzodiazepine As described for example 29) using freshly prepared cyclopropylzinc chloride solution (0.38 M in THF) instead of diethylzinc solution, 3-bromo-10-chloro-9H-imidazo[1,5-a][1,2,4]triazolo[1,5-d][1,4]benzodiazepine (200 mg, 0.59 mmol) was converted to the title compound (SiO$_2$, heptane: ethyl acetate=50:50 to 40:60, 118 mg, 67%) which was obtained as a white solid. MS: m/e=298.0 [M+H]$^+$.

EXAMPLE 31

10-Chloro-3-cyclopentyl-9H-imidazo[1,5-a][1,2,4]triazolo[1,5-d][1,4]benzodiazepine As described for example 29) using cyclopentylzinc bromide solution (0.5 M in THF) instead of diethylzinc solution, 3-bromo-10-chloro-9H-imidazo[1,5-a][1,2,4]triazolo[1,5-d][1,4]benzodiazepine (166 mg, 0.49 mmol) was converted to the title compound (SiO$_2$, heptane:ethyl acetate:dichloromethane=6:2:2 to 3:5:2, 19 mg, 12%) which was obtained as a white solid. MS: m/e=326.2 [M+H]$^+$.

EXAMPLE 32

10-Chloro-3-difluoromethyl-9H-imidazo[1,5-a][1,2,4]triazolo[1,5-d][1,4]benzodiazepine a) 10-Chloro-3-formyl-9H-imidazo[1,5-a][1,2,4]triazolo[1,5-d][1,4]benzodiazepine A suspension of 3-bromo-10-chloro-9H-imidazo[1,5-a][1,2,4]triazolo[1,5-d][1,4]benzodiazepine (448 mg, 1.33 mmol), bis(triphenylphosphine)palladium(II) chloride (19 mg, 0.03 mmol) and sodium formate (136 mg, 2.00 mmol) in DMF (8 mL) was stirred for 4 h at 110° C. under a carbon monoxide atmospere. Further bis(triphenylphosphine)palladium(II) chloride (19 mg, 0.03 mmol) and sodium formate (136 mg, 2.00 mmol) was added and stirring was continued for further 2 h under a carbon monoxide atmosphere. The reaction mixture was diluted with ethyl acetate (30 mL) and washed with aqueous Na$_2$CO$_3$ (sat.), water and aqueous Na$_2$CO$_3$ (sat.). The aqueous layers were extracted with ethyl acetate (30 mL) and dried over sodium sulfate. Purification by chromatography (SiO$_2$, dichloromethane:methanol=99:1 to 95:5) afforded the title compound (194 mg, 51%) as a white solid. MS: m/e=318.1 [M+MeOH+H]$^+$.

b) 10-Chloro-3-difluoromethyl-9H-imidazo[1,5-a][1,2,4]triazolo[1,5-d][1,4]benzodiazepine A mixture of 10-chloro-3-formyl-9H-imidazo[1,5-a][1,2,4]triazolo[1,5-d][1,4]benzodiazepine (192 mg, 0.67 mmol) and bis(2-methoxyethyl)aminosulphur trifluoride (163 µl, 1.61 mmol) in dichloromethane (4 mL) was stirred for 2 h at ambient temperature. Further bis(2-mrethoxyethyl)aminosulphur trifluoride (163 µL, 1.61 mmol) was added and stirring was continued for another 16 h. The reaction mixture was diluted with ethyl acetate (20 mL), washed with aqueous Na$_2$CO$_3$ (sat.) and extracted with ethyl acetate (20 mL). Drying over sodium sulfate and purification by chromatography (SiO$_2$, heptane:ethyl acetate:dichloromethane=6:2:2 to 3:5:2) afforded the title compound (136 mg, 66%) as a white solid. MS: m/e=308.2 [M+H]$^+$.

EXAMPLE 33

3-Benzyl-10-chloro-9H-imidazo[1,5-a][1,2,4]triazolo[1,5-d][1,4]benzodiazepine

As described for example 29) using benzylzinc bromide solution (0.5 M in THF) instead of diethylzinc solution, 3-bromo-10-chloro-9H-imidazo[1,5-a][1,2,4]triazolo[1,5-d][1,4]benzodiazepine (238 mg, 0.71 mmol) was converted to the title compound (SiO$_2$, heptane:ethyl acetate:dichloromethane=6:2:2 to 3:5:2, 117 mg, 48%) which was obtained as an off-white solid. MS: m/e=348.0 [M+H]$^+$.

EXAMPLE 34

10-Chloro-3-phenyl-9H-imidazo[1,5-a][1,2,4]triazolo[1,5-d][1,4]benzodiazepine

As described for example 29) using phenylzinc iodide solution (0.5 M in THF) instead of diethylzinc solution, 3-bromo-10-chloro-9H-imidazo[1,5-a][1,2,4]triazolo[1,5-d][1,4]benzodiazepine (257 mg, 0.76 mmol) was converted to the title compound (SiO$_2$, heptane:ethyl acetate:dichloromethane=6:2:2 to 3:5:2, 43 mg, 17%) which was obtained as an off-white solid. MS: m/e=334.0 [M+H]$^+$.

EXAMPLE 35

10-Chloro-3-cyano-9H-imidazo[1,5-a][1,2,4]triazolo[1,5-d][1,4]benzodiazepine

A mixture of 3-bromo-10-chloro-9H-imidazo[1,5-a][1,2,4]triazolo[1,5-d][1,4]benzodiazepine (200 mg, 0.59 mmol) and copper(I) cyanide (106 mg, 1.19 mmol) in 1-methyl-2-pyrrolidone (2 mL) was stirred for 3 h at 160° C. followed by stirring for 3 h at 210° C. The reaction mixture was diluted with ethyl acetate (20 mL), washed with aqueous Na$_2$CO$_3$ (sat.), water and again aqueous Na$_2$CO$_3$ (sat.). The aqueous layers were extracted with ethyl acetate (30 mL). Drying over sodium sulfate and purification by chromatography (SiO$_2$, heptane:ethyl acetate:dichloromethane=7:2:1 to 4:5:1) afforded the title compound (50 mg, 30%) as an off-white solid. MS: m/e=283.0 [M+H]$^+$.

EXAMPLE 36

3,10-Dichloro-6-methyl-9H-imidazo[1,5-a][1,2,4]triazolo[1,5-d][1,4]benzodiazepine a) 4-Chloro-2-cyano-phenyl)-carbamic acid ethyl ester As described for example 21a) 2-amino-5-chlorobenzonitrile (33.4 g, 219 mmol), instead of 2-amino-5-bromobenzonitrile, was converted to the title compound (46.9 g, 95%) which was obtained as a light yellow solid. MS: m/e=242.3 [M+NH$_4$]$^+$.

b) 9-Chloro-2-methyl-6H-[1,2,4]triazolo[1,5-c]quinazolin-5-one

As described for example 21b) 4-chloro-2-cyano-phenyl)-carbamic acid ethyl ester (10.0 g, 44.5 mmol), instead of 4-bromo-2-cyano-phenyl)-carbamic acid ethyl ester, using acetic acid hydrazide instead of formylhydrazine, was converted to the title compound (9.81 g, 94%) which was obtained as a light yellow solid. MS: m/e=234.9 [M]$^+$.

c) 4-Chloro-2-(5-methyl-2H-[1,2,4]triazol-3-yl)-phenylamine

As described for example 21c) 9-chloro-2-methyl-6H-[1,2,4]triazolo[1,5-c]quinazolin-5-one (9.67 g, 41.2 mmol), instead of 9-bromo-6H-[1,2,4]triazolo[1,5-c]quinazolin-5-one, was converted to the title compound (6.57 g, 76%) which was obtained as an off-white solid. MS: m/e=209.0 [M+H]$^+$.

d) 9-Chloro-2-methyl-6H-1,3,3a,6-tetraaza-benzo[e]azulen-5-one

As described for example 21d) 4-chloro-2-(5-methyl-2H-[1,2,4]triazol-3-yl)-phenylamine (9.44 g, 30.9 mmol), instead of 4-bromo-2-(2H-[1,2,4]triazol-3-yl)-phenylamine, was converted to the title compound (4.83 g, 63%) which was obtained as a white solid. MS: m/e=248.9 [M]$^+$.

e) Ethyl 3-chloro-6-methyl-9H-imidazo[1,5-a][1,2,4]triazolo[1,5-d][1,4]benzodiazepine-10-carboxylate As described for example 21e) 9-chloro-2-methyl-6H-1,3,3a,6-tetraaza-benzo[e]azulen-5-one (2.49 g, 10.0 mmol) instead of 9-bromo-6H-1,3,3a,6-tetraaza-benzo[e]azulen-5-one was converted to the title compound (1.19 g, 35%) which was obtained as a light brown solid. MS: m/e=344.0 [M+H]$^+$.

f) 3-Chloro-6-methyl-9H-imidazo[1,5-a][1,2,4]triazolo[1,5-d][1,4]benzodiazepine

A mixture of ethyl 3-chloro-6-methyl-9H-imidazo[1,5-a][1,2,4]triazolo[1,5-d][1,4]benzo-diazepine-10-carboxylate (800 mg, 2.33 mmol), ethanol (10 mL) and aqueous sodium hydroxide (1 N, 9.31 mL, 9.31 mmol) was stirred for 30 min at 80° C. The mixture was evaporated and the residue was dissolved in water(10 mL) and adjusted to pH=1.5 with aqueous HCl (1 N, 9 mL). The resulting suspension was stirred for 30 min at 0° C., filtered, washed with water (20 mL) and dried in vacuo. The pale yellow solid was suspended in diethylene glycol dibutyl ether (3.0 mL) and stirred for 88 h at 200° C. under a nitrogen atmosphere. The suspension was treated with heptane (15 mL) and stirred for 30 min at 0° C., filtered off and washed with heptane (5 mL). Drying in vacuo afforded the title compound (409 mg, 65%) as a light brown solid. MS: m/e=272.0 [M+H]$^+$.

g) 3,10-Dichloro-6-methyl-9H-imidazo[1,5-a][1,2,4]triazolo[1,5-d][1,4]benzodiazepine As described for example 2b) 3-chloro-6-methyl-9H-imidazo[1,5-a][1,2,4]triazolo[1,5-d][1,4]benzodiazepine (300 mg, 1.10 mmol), instead of 3-fluoro-9H-imidazo[1,5-a][1,2,4,]-triazolo[1,5-d][1,4]-benzodiazepine, was converted to the title compound (SiO$_2$, heptane:ethyl acetate:dichloromethane=75:15:10 to 0:90:10, 106 mg, 31%) which was obtained as an off-white solid. MS: m/e=306.1 [M]$^+$.

EXAMPLE 37

3,10-Dichloro-6-phenyl-9H-imidazo[1,5-a][1,2,4]triazolo[1,5-d][1,4]benzodiazepine a) 9-Chloro-2-phenyl-6H-[1,2,4]triazolo[1,5-c]quinazolin-5-one As described for example 21b) 4-chloro-2-cyano-phenyl)-carbamic acid ethyl ester (5.00 g, 22.3 mmol), instead of 4-bromo-2-cyano-phenyl)-carbamic acid ethyl ester, using benzoylhydrazine instead of formylhydrazine, was converted to the title compound (6.50 g, 98%) which was obtained as an off-white solid. MS: m/e=297.1 [M+H]$^+$.

b) 4-Chloro-2-(5-phenyl-2H-[1,2,4]triazol-3-yl)-phenylamine

As described for example 21c) 9-chloro-2-phenyl-6H-[1,2,4]triazolo[1,5-c]quinazolin-5-one (6.34 g, 21.4 mmol), instead of 9-bromo-6H-[1,2,4]triazolo[1,5-c]quinazolin-5-one, was converted to the title compound (5.35 g, 92%) which was obtained as a light brown solid. MS: m/e=271.0 [M+H]$^+$.

c) 9-Chloro-2-phenyl-6H-1,3,3a,6-tetraaza-benzo[e]azulen-5-one

As described for example 21d) 4-chloro-2-(5-phenyl-2H-[1,2,4]triazol-3-yl)-phenylamine (5.24 g, 19.3 mmol), instead of 4-bromo-2-(2H-[1,2,4]triazol-3-yl)-phenylamine, was converted to the title compound (4.40 g, 73%) which was obtained as an off-white solid. MS: m/e=311.0 [M+H]$^+$.

d) Ethyl 3-chloro-6-phenyl-9H-imidazo[1,5-a][1,2,4]triazolo[1,5-d][1,4]benzodiazepine-10-carboxylate As described for example 21e) 9-chloro-2-phenyl-6H-1,3,3a,6-tetraaza-benzo[e]azulen-5-one (3.11 g, 10.0 mmol) instead of 9-bromo-6H-1,3,3a,6-tetraaza-benzo[e]azulen-5-one was converted to the title compound (1.26 g, 31%) which was obtained as a light yellow solid. MS: m/e=406.2 [M+H]$^+$.

e) 3-Chloro-6-phenyl-9H-imidazo[1,5-a][1,2,4]triazolo[1,5-d][1,4]benzodiazepine

As described for example 36f) ethyl 3-chloro-6-phenyl-9H-imidazo[1,5-a][1,2,4]triazolo[1,5-d][1,4]benzodiazepine-10-carboxylate (1.00 g, 2.46 mmol) instead of ethyl 3-chloro-6-methyl-9H-imidazo[1,5-a][1,2,4]triazolo[1,5-d][1,4]benzodiazepine-10-carboxylate was converted to the title compound (727 mg, 88%) which was obtained as an off-white solid. MS: m/e=334.2 [M+H]$^+$.

f) 3,10-Dichloro-6-phenyl-9H-imidazo[1,5-a][1,2,4]triazolo[1,5-d][1,4]benzodiazepine As described for example 2b) 3-chloro-6-phenyl-9H-imidazo[1,5-a][1,2,4]triazolo[1,5-d][1,4]benzodiazepine (500 mg, 1.50 mmol), instead of 3-fluoro-9H-imidazo[1,5-a][1,2,4]-triazolo[1,5-d][1,4]-benzodiazepine, was converted to the title compound (SiO$_2$, heptane:ethyl acetate:dichloromethane=85:5:10 to 25:65:10, 124 mg, 22%) which was obtained as a light yellow solid. MS: m/e=368.1 [M]$^+$.

EXAMPLE 38

3-Bromo-10-chloro-6-methyl-9H-imidazo[1,5-a][1,2,4]triazolo[1,5-d][1,4]benzodiazepine a) 3-Bromo-2-methyl-6H-[1,2,4]triazolo[1,5-c]quinazolin-5-one As described for example 21b) 4-bromo-2-cyano-phenyl)-carbamic acid ethyl ester (30.0 g, 111 mmol), using acetic acid hydrazide instead of formylhydrazine, was converted to the title compound (28.5 g, 91%) which was obtained as an off-white solid. MS: m/e=277.0/279.1 [M−H]$^-$.

b) 4-Bromo-2-(5-methyl-2H-[1,2,4]triazol-3-yl)-phenylamine

As described for example 21c) 9-bromo-2-methyl-6H-[1,2,4]triazolo[1,5-c]quinazolin-5-one (28.5 g, 102 mmol), instead of 9-bromo-6H-[1,2,4]triazolo[1,5-c]quinazolin-5-one, was converted to the title compound (25.5 g, 99%) which was obtained as an off-white solid. MS: m/e=251.0/253.1 [M−H]$^-$.

c) 9-Bromo-2-methyl-6H-1,3,3a,6-tetraaza-benzo[e]azulen-5-one

As described for example 21d) 4-bromo-2-(5-methyl-2H-[1,2,4]triazol-3-yl)-phenylamine (24.9 g, 98.3 mmol), instead of 4-bromo-2-(2H-[1,2,4]triazol-3-yl)-phenylamine, was converted to the title compound (17.0 g, 59%) which was obtained as an off-white solid. MS: m/e=291.0/293.2 [M−H]$^-$.

d) Ethyl 3-bromo-6-methyl-9H-imidazo[1,5-a][1,2,4]triazolo[1,5-d][1,4]benzodiazepine-10-carboxylate As described for example 21e) 9-bromo-2-methyl-6H-1,3,3a,6-tetraaza-benzo[e]azulen-5-one (16.8 g, 57.3 mmol) instead of 9-bromo-6H-1,3,3a,6-tetraaza-benzo[e]azulen-5-one was converted to the title compound (14.7 g, 66%) which was obtained as an off-white solid. MS: m/e=388.2/390.1 [M+H]$^+$.

e) 3-Bromo-6-methyl-9H-imidazo[1,5-a][1,2,4]triazolo[1,5-d][1,4]benzodiazepine-10-carboxylic acid As described for example 21f) ethyl 3-bromo-6-methyl-9H-imidazo[1,5-a][1,2,4]triazolo[1,5-d][1,4]benzodiazepine-10-carboxylate (11.5 g, 29.5 mmol) instead of ethyl 3-bromo-9H-imidazo[1,5-a][1,2,4]triazolo[1,5-d][1,4]benzodiazepine-10-carboxylate was converted to the title compound (3.46 g, 33%) which was obtained as a light brown solid. MS: m/e=358.1/360.2 [M–H]$^-$.

f) 3-Bromo-6-methyl-9H-imidazo[1,5-a][1,2,4]triazolo[1,5-d][1,4]benzodiazepine

As described for example 2a) 3-bromo-6-methyl-9H-imidazo[1,5-a][1,2,4]triazolo[1,5-d][1,4]benzodiazepine-10-carboxylic acid (3.39 g, 9.41 mmol) instead of 3-fluoro-9H-imidazo[1,5-a][1,2,4]triazolo[1,5-d][1,4]benzodiazepine-10-carboxylic acid was converted to the title compound (2.12 mg, 71%) which was obtained as a light brown solid. MS: m/e=316.0/319.9 [M+H]$^+$.

g) 3-Bromo-10-chloro-6-methyl-9H-imidazo[1,5-a][1,2,4]triazolo[1,5-d][1,4]benzodiazepine As described for example 2b) 3-chloro-6-methyl-9H-imidazo[1,5-a][1,2,4]triazolo[1,5-d][1,4]benzodiazepine (200 mg, 0.63 mmol), instead of 3-fluoro-9H-imidazo[1,5-a][1,2,4]-triazolo[1,5-d][1,4]-benzodiazepine, was converted to the title compound (SiO$_2$, heptane:ethyl acetate:dichloromethane=7:2:1 to 4:5:1, 88 mg, 40%) which was obtained as a white solid. MS: m/e 349.9/351.9 [M]$^+$.

EXAMPLE 39

10-Chloro-6-methyl-3-trimethylsilanylethynyl-9H-imidazo[1,5-a][1,2,4]triazolo[1,5-d][1,4]benzodiazepine As described for example 23, 3-bromo-10-chloro-6-methyl-9H-imidazo[1,5-a][1,2,4]triazolo-[1,5-d][1,4]benzodiazepine (400 mg, 1.14 mmol), instead of 3-bromo-10-chloro-9H-imidazo[1,5-a][1,2,4]triazolo[1,5-d][1,4] benzodiazepine, was converted to the title compound (SiO$_2$, heptane:ethyl acetate:dichloromethane=9:1:0 to 4:5:1, 374 mg, 89%) which was obtained as an off-white solid. MS: m/e=368.2 [M+H]$^+$.

EXAMPLE 40

10-Chloro-3-ethynyl-6-methyl-9H-imidazo[1,5-a][1,2,4]triazolo[1,5-d][1,4]benzodiazepine As described for example 24, 10-chloro-6-methyl-3-trimethylsilanylethynyl-9H-imidazo[1,5-a][1,2,4]triazolo[1,5-d][1,4]benzodiazepine (450 mg, 1.22 mmol), instead of 10-chloro-3-trimethylsilanylethynyl-9H-imidazo[1,5-a][1,2,4]triazolo[1,5-d][1,4]benzodiazepine, was converted to the title compound (SiO$_2$, heptane:ethyl acetate:dichloromethane=7:2:1 to 4:5:1, 153 mg, 42%) which was obtained as a white solid. MS: m/e=296.1 [M+H]$^+$.

EXAMPLE 41

10-Chloro-3-cyclopropyl-6-methyl-9H-imidazo[1,5-a][1,2,4]triazolo[1,5-d][1,4]benzodiazepine As described for example 29, using freshly prepared cyclopropylzinc chloride solution (0.38 M in THF) instead of diethylzinc solution, 3-bromo-10-chloro-6-methyl-9H-imidazo[1,5-a][1,2,4]triazolo[1,5-d][1,4]benzodiazepine (500 mg, 1.43 mmol) instead of 3-bromo-10-chloro-9H-imidazo[1,5-a][1,2,4]triazolo[1,5-d][1,4]benzodiazepine was converted to the title compound (SiO$_2$, heptane:ethyl acetate:dichloromethane=25:45:20, 168 mg, 38%) which was obtained as a white solid. MS: m/e=312.2 [M+H]$^+$.

EXAMPLE 42

10-Chloro-3-cyano-6-methyl-9H-imidazo[1,5-a][1,2,4]triazolo[1,5-d][1,4]benzodiazepine As described for example 35, 3-bromo-10-chloro-6-methyl-9H-imidazo[1,5-a][1,2,4]triazolo[1,5-d][1,4]benzodiazepine (200 mg, 0.57 mmol) instead of 3-bromo-10-chloro-9H-imidazo[1,5-a][1,2,4]triazolo[1,5-d][1,4] benzodiazepine was converted to the title compound (SiO$_2$, heptane:ethyl acetate:dichloromethane=7:2:1 to 4:5:1, 66 mg, 39%) which was obtained as a white solid. MS: m/e=297.1 [M+H]$^+$.

EXAMPLE 43

10,12-Dichloro-3-methoxy-9H-imidazo[1,5-a][1,2,4]triazolo[1,5-d][1,4]benzodiazepine To a solution of 3-methoxy-9H-imidazo[1,5-a][1,2,4]triazolo[1,5-d][1,4]benzodiazepine (200 mg, 0.79 mmol) in DMF (3 mL) was added N-chlorosuccinimide (116 mg, 0.87 mmol) and the resulting suspension was stirred for 14 d at ambient temperature. The mixture was diluted with ethyl acetate (20 mL) and washed with aqueous sodium carbonate (2 N). After re-extraction with ethyl acetate (20 mL), the combined layers were washed with water (20 mL) and dried over sodium sulfate. Purification by chromatography (SiO$_2$, heptane:ethyl acetate:dichloromethane=7:2:1 to 4:5:1) afforded the title compound (64 mg, 25%) as awhite solid. MS: m/e=322.2 [M]$^+$.

EXAMPLE 44

10,12-Dichloro-3-ethoxy-9H-imidazo[1,5-a][1,2,4]triazolo[1,5-d][1,4]benzodiazepine To a solution of 3-ethoxy-9H-imidazo[1,5-a][1,2,4]triazolo[1,5-d][1,4]benzodiazepine (200 mg, 0.75 mmol) in DMF (2 mL) was added at ambient temperature 1,3-dichloro-5,5-dimethylhydantoin (81 mg, 0.41 mmol) and stirred for 24 h. Another portion of 1,3-dichloro-5,5-dimethylhydantoin (40 mg, 0.15 mmol) was added and stirring was continued for further 18 h at ambient tempreature. The mixture was diluted with ethyl acetate (20 mL), washed with aqueous sodium carbonate and dried over sodium sulfate. Purification by chromatography (SiO$_2$, heptane:ethyl acetate:dichloromethane=6:2:2 to 3:5:2) afforded the title compound (50 mg, 20%) as a light brown solid. MS: m/e=336.0 [M]$^+$.

EXAMPLE 45

10,12-Dichloro-3-methyl-9H-imidazo[1,5-a][1,2,4]triazolo[1,5-d][1,4]benzodiazepine As described for example 2b), 3-methyl-9H-imidazo[1,5-a][1,2,4]triazolo[1,5-d][1,4]benzo-diazepine (210 mg, 0.89 mmol), instead of 3-fluoro-9H-imidazo[1,5-a][1,2,4]triazolo[1,5-d][1,4]-benzodiazepine, was converted to the title compound (SiO$_2$, heptane:ethyl acetate:dichloromethane=7:2:1 to 4:5:1, 45 mg, 17%) which was obtained as a white solid. MS: m/e=306.1 [M]$^+$.

EXAMPLE 46

10-Bromo-9H-imidazo[1,5-a][1,2,4]triazolo[1,5-d][1,4]benzodiazepine

To a solution of 9H-imidazo[1,5-a][1,2,4]triazolo[1,5-d][1,4]benzodiazepine (690 mg, 3.09 mmol) in dimethylformamide (15 mL) was added bromine (0.48 mL, 9.3 mmol). The resulting solution was stirred for 48 h at 50° C. before aqueous NaHCO$_3$ (sat.) was added and the the mixture extracted with dichloromethane. Drying over sodium sulfate and purification by chromatography (SiO$_2$, dichloromethane:ethanol=100:0 to 97:3) afforded the title compound (265 mg, 28%) as a white crystalline solid. MS: m/e=302.0/304.0 [M+H]$^+$.

EXAMPLE 47

10-Bromo-3-fluoro-9H-imidazo[1,5-a][1,2,4]triazolo[1,5-d][1,4]benzodiazepine As described for example 46, 3-fluoro-9H-imidazo[1,5-a][1,2,4]triazolo[1,5-d][1,4]benzo-diazepine (482 mg, 2.00 mmol), instead of 9H-imidazo[1,5-a][1,2,4]triazolo[1,5-d][1,4]-benzodiazepine, was converted to the title compound (SiO$_2$, dichloromethane:ethanol=100:1 to 97:3, 170 mg, 27%) which was obtained as a white solid. MS: m/e=319.9/321.9 [M]$^+$.

EXAMPLE 48

3-Chloro-10-iodo-9H-imidazo[1,5-a][1,2,4]triazolo[1,5-d][1,4]benzodiazepine

To a solution of 3-chloro-9H-imidazo[1,5-a][1,2,4]triazolo[1,5-d][1,4]benzodiazepine (7.40 g, 28.7 mmol) in dimethylformamide (240 mL) was added iodine (14.6 g, 57.5 mmol). The resulting mixture was stirred for 6 d at 55° C. before water (3 L) and aqueous Na$_2$S$_2$O$_3$ (10%, mL) were added and the the mixture extracted with dichloromethane. Drying over sodium sulfate and purification by chromatography (SiO$_2$, dichloromethane:ethanol=100:0 to 97:3) afforded the title compound (3.10 g, 35%) as a white crystalline solid. MS: m/e=383.9 [M]$^+$.

EXAMPLE 49

3-Methanesulfonylamino-10-chloro-9H-imidazo[1,5-a][1,2,4]triazolo[1,5-d][1,4]benzodiazepine To a solution of methane sulfonamide (690 mg, 7.26 mmol) in DMSO (6 mL) was added sodium hydride (55% dispersion in mineral oil, 253 mg, 5.80 mmol) at 0° C. After stirring for 2 h at ambient temperature 3-fluoro-10-chloro-9H-imidazo[1,5-a][1,2,4]triazolo[1,5-d][1,4]benzodiazepine (400 mg, 1.45 mmol) was added and the reaction mixture was stirred successively for 2 h at 80° C., 2 h at 130° C. and 17 h at 170° C. After cooling to ambient temperature the reaction mixture was treated with acetic acid (0.5 mL), water (20 mL) and dichloromethane (30 mL) and was stirred for 10 min. The organic layer was washed with water and was dried over sodium sulfate. Purification by chromatography (SiO$_2$, dichloromethane:methanol=10:0 to 9:1) afforded the title compound (126 mg, 25%) as a white solid. MS: m/e=351.2 [M]$^+$.

EXAMPLE 50

3-(Cyclopropanecarbonyl-amino)-10-chloro-9H-imidazo[1,5-a][1,2,4]triazolo[1,5-d][1,4]benzodiazepine As described for example 49, 10-chloro-3-fluoro-9H-imidazo[1,5-a][1,2,4]triazolo[1,5-d][1,4]-benzodiazepine (400 mg, 1.45 mmol) was converted using cyclopropanecarboxamide instead of methane sulfonamide to the title compound (SiO$_2$, heptane:ethyl acetate:dichloromethane=40:40:20 to 0:80:20, 36 mg, 7%) which was obtained as a white solid. MS: m/e=341.1 [M+H]$^+$.

EXAMPLE 51

10-Chloro-3-(3,4-difluoro-phenyl)-9H-imidazo[1,5-a][1,2,4]triazolo[1,5-d][1,4]benzodiazepine To a solution of 3-bromo-10-chloro-9H-imidazo[1,5-a][1,2,4]triazolo[1,5-d][1,4]benzodiazepine (200 mg, 0.59 mmol), tetrakis(triphenylphosphine)palladium(0) (7 mg, 0.006 mmol), 3,4-difluorophenylboronic acid (103 mg, 0.65 mmol) and aqueous sodium hydrogen carbonate (1N, 1.4 mL, 1.4 mmol) in 1,2-dimethoxyethane (2 mL) was stirred for 2 h at 100° C. under an argon atmosphere. The reaction mixture was diluted with dichloromethane (10 mL) and was washed with water (10 mL) and aqueous sodium carbonate (10 mL). Drying over sodium sulfate, concentration and washing with water (10 mL) and 1,2-dimethoxyethane (10 mL) afforded the title compound (139 mg, 63%) as an off-white solid. MS: m/e=370.0 [M+H]$^+$.

EXAMPLE 52

10-Chloro-3-(3,5-bis-trifluoromethyl-phenyl)-9H-imidazo[1,5-a][1,2,4]triazolo[1,5-d][1,4]benzodiazepine As described for example 52, 3-bromo-10-chloro-9H-imidazo[1,5-a][1,2,4]triazolo[1,5-d][1,4]-benzodiazepine (200 mg, 0.59 mmol) was converted using 3,5-bis-trifluoromethyl-benzeneboronic acid instead of difluorophenylboronic acid to the title compound (160 mg, 57%) which was obtained as a white solid. MS: m/e=470.3 [M+H]$^+$.

EXAMPLE 53

10-Chloro-3-(2-fluoro-phenyl)-9H-imidazo[1,5-a][1,2,4]triazolo[1,5-d][1,4]benzodiazepine As described for example 51, 3-bromo-10-chloro-9H-imidazo[1,5-a][1,2,4]triazolo[1,5-d][1,4]-benzodiazepine (200 mg, 0.59 mmol) was converted using 2-fluoro-benzeneboronic acid instead of difluorophenylboronic acid to the title compound (128 mg, 61%) which was obtained as an off-white solid. MS: m/e=352.2 [M+H]$^+$.

EXAMPLE 54

10-Chloro-3-(2,4-difluorobenzyl)-9H-imidazo[1,5-a][1,2,4]triazolo[1,5-d][1,4]benzodiazepine As described for example 29, 3-bromo-10-chloro-9H-imidazo[1,5-a][1,2,4]triazolo[1,5-d][1,41]-benzodiazepine (200 mg, 0.59 mmol) was converted using 2,4-difluorobenzylzinc bromide solution (0.5 M in THF) instead of diethylzinc solution to the title compound (142 mg, 62%) which was obtained as a light brown solid. MS: m/e=384.1 [M+H]$^+$.

EXAMPLE 55

10-Chloro-3-(3,4-difluorobenzyl)-9H-imidazo[1,5-a][1,2,4]triazolo[1,5-d][1,4]benzodiazepine As described for example 29, 3-bromo-10-chloro-9H-imidazo[1,5-a][1,2,4]triazolo[1,5-d][1,4]-benzodiazepine (200 mg, 0.59 mmol) was converted using 3,4-difluorobenzylzinc bromide solution (0.5 M in THF) instead of diethylzinc solution to the title compound (86 mg, 38%) which was obtained as a light brown solid. MS: m/e=384.1 $[M+H]^+$.

EXAMPLE 56

10-Chloro-3-(pyridin-4-yl)-9H-imidazo[1,5-a][1,2,4]triazolo[1,5-d][1,4]benzodiazepine As described for example 51, 3-bromo-10-chloro-9H-imidazo[1,5-a][1,2,4]triazolo[1,5-d][1,4]-benzodiazepine (400 mg, 1.19 mmol) was converted using pyridin-4-ylboronic acid instead of difluorophenylboronic acid to the title compound (295 mg, 74%) which was obtained as a white solid. MS: m/e=335.0 $[M+H]^+$.

EXAMPLE 57

10-Chloro-3-(pyridin-3-yl)-9H-imidazo[1,5-a][1,2,4]triazolo[1,5-d][1,4]benzodiazepine As described for example 51, 3-bromo-10-chloro-9H-imidazo[1,5-a][1,2,4]triazolo[1,5-d][1,4]-benzodiazepine (400 mg, 1.19 mmol) was converted using pyridin-3-ylboronic acid instead of difluorophenylboronic acid to the title compound (205 mg, 52%) which was obtained as a grey solid. MS: m/e=335.0 $[M+H]^+$.

EXAMPLE 58

10-Chloro-3-(2-tolyl)-9H-imidazo[1,5-a][1,2,4]triazolo[1,5-d][1,4]benzodiazepine As described for example 51, 3-bromo-10-chloro-9H-imidazo[1,5-a][1,2,4]triazolo[1,5-d][1,4]-benzodiazepine (300 mg, 0.89 mmol) was converted using 2-tolylboronic acid instead of difluorophenylboronic acid to the title compound (300 mg, 97%) which was obtained as a grey solid. MS: m/e=347.1 $[M]^+$.

EXAMPLE 59

3-(3-Amino-phenyl)-10-chloro-9H-imidazo[1,5-a][1,2,4]triazolo[1,5-d][1,4]benzodiazepine As described for example 51, 3-bromo-10-chloro-9H-imidazo[1,5-a][1,2,4]triazolo[1,5-d][1,4]-benzodiazepine (400 mg, 1.19 mmol) was converted using 3-amino-phenylboronic acid instead of difluorophenylboronic acid to the title compound (300 mg, 72%) which was obtained as a white solid. MS: m/e=349.1 $[M+H]^+$.

EXAMPLE 60

10-Chloro-3-(2-methoxy-phenyl)-9H-imidazo[1,5-a][1,2,4]triazolo[1,5-d][1,4]benzodiazepine As described for example 51, 3-bromo-10-chloro-9H-imidazo[1,5-a][1,2,4]triazolo[1,5-d][1,4]-benzodiazepine (400 mg, 1.19 mmol) was converted using 2-methoxy-phenylboronic acid instead of difluorophenylboronic acid to the title compound (396 mg, 92%) which was obtained as a light yellow solid. MS: m/e=363.1 $[M]^+$.

EXAMPLE 61

10-Chloro-3-(3-methoxy-phenyl)-9H-imidazo[1,5-a][1,2,4]triazolo[1,5-d][1,4]benzodiazepine As described for example 51, 3-bromo-10-chloro-9H-imidazo[1,5-a][1,2,4]triazolo[1,5-d][1,4]-benzodiazepine (300 mg, 0.89 mmol) was converted using 3-methoxy-phenylboronic acid instead of difluorophenylboronic acid to the title compound (292 mg, 90%) which was obtained as an off-white solid. MS: m/e=363.1 $[M]^+$.

EXAMPLE 62

10-Chloro-3-(4-tolyl)-9H-imidazo[1,5-a][1,2,4]triazolo[1,5-d][1,4]benzodiazepine As described for example 51, 3-bromo-10-chloro-9H-imidazo[1,5-a][1,2,4]triazolo[1,5-d][1,4]-benzodiazepine (300 mg, 0.89 mmol) was converted using 4-tolylboronic acid instead of difluorophenylboronic acid to the title compound (261 mg, 84%) which was obtained as a grey solid. MS: m/e=347.1 $[M]^+$.

EXAMPLE 63

3-(Benzo[1,3]dioxol-5-yl)-10-chloro-9H-imidazo[1,5-a][1,2,4]triazolo[1,5-d][1,4]benzodiazepine As described for example 51, 3-bromo-10-chloro-9H-imidazo[1,5-a][1,2,4]triazolo[1,5-d][1,4]-benzodiazepine (300 mg, 0.89 mmol) was converted using 4-tolylboronic acid instead of difluorophenylboronic acid to the title compound (266 mg, 79%) which was obtained as a white solid. MS: m/e=377.1 $[M]^+$.

EXAMPLE 64

10-Chloro-3-propyl-9H-imidazo[1,5-a][1,2,4]triazolo[1,5-d][1,4]benzodiazepine

As described for example 29, 3-bromo-10-chloro-9H-imidazo[1,5-a][1,2,4]triazolo[1,5-d][1,4]-benzodiazepine (200 mg, 0.59 mmol) was converted using diisopropyl zinc solution (1 M in toluene) instead of diethylzinc solution to the title compound (112 mg, 63%) which was obtained as a white solid. MS: m/e=300.4 $[M+H]^+$.

EXAMPLE 65

3-Butyl-10-chloro-9H-imidazo[1,5-a][1,2,4]triazolo[1,5-d][1,4]benzodiazepine

As described for example 29, 3-bromo-10-chloro-9H-imidazo[1,5-a][1,2,4]triazolo[1,5-d][1,4]-benzodiazepine (200 mg, 0.59 mmol) was converted using cyclopropyl zinc bromide solution (0.29 M in THF) instead of diethylzinc solution to the title compound (34 mg, 18%) which was obtained as a white solid. MS: m/e=314.1 $[M+H]^+$.

EXAMPLE 66

10-Chloro-3-vinyl-9H-imidazo[1,5-a][1,2,4]triazolo[1,5-d][1,4]benzodiazepine To a suspension of 3-bromo-10-chloro-9H-imidazo[1,5-a][1,2,4]triazolo[1,5-d][1,4]-benzodiazepine (200 mg, 0.59 mmol) in toluene (2 mL) was added under an argon atmosphere vinyl tributyltin (0.21 mL, 0.71 mmol), tetrakis(triphenylphosphine)palladium (0) (34 mg, 0.03 mmol) and 2,6-di-tert.-butyl-4-methylphenol (some crystals). The resulting mixture was stirred for 18 h at 100° C. It was diluted with dichloromethane and washed with aqueous sodium carbonate (half saturated), with water and extracted with dichloromethane. Drying over sodium sulfate and purification by chromatography ($SiO_2$, heptane:ethyl acetate:dichloromethane 60:20:20 to 30:50:20) afforded the title compound (145 mg, 86%) as a white solid. MS: m/e=284.1 [M]$^+$.

EXAMPLE 67

3-(Bicyclo[2.2.1]hept-5-en-2-yl)-10-chloro-9H-imidazo[1,5-a][1,2,4]triazolo[1,5-d][1,4]benzodiazepine 10-Chloro-3-vinyl-9H-imidazo[1,5-a][1,2,4]triazolo[1,5-d][1,4]benzodiazepine (200 mg, 0.71 mmol) was dissolved in warm THF (10 mL). After cooling to ambient temperature diclyclopentadiene (95 µl; 0.71 mmol) was added and the reaction mixture was stirred for 18 h at this temperature. Further dicyclopentadiene (0.48 mL, 0.36 mmol) was added and the THF was distilled off. The resulting suspension was stirred for 18 h at 160° C. under a nitrogen atmosphere and concentrated. Purification by chromatography ($SiO_2$, heptane:ethyl acetate:dichloromethane=60:20:20 to 30:50:20) afforded the title compound (93 mg, 38%) as a white foam. MS: m/e=350.1[M+H]$^+$.

EXAMPLE 68

10-Chloro-3-trimethylsilyl-9H-imidazo[1,5-a][1,2,4]triazolo[1,5-d][1,4]benzodiazepine A solution of 3-bromo-10-chloro-9H-imidazo[1,5-a][1,2,4]triazolo[1,5-d][1,4]-benzodiazepine (200 mg, 0.59 mmol) in 1,3-dimethyl-3,4,5,6-tetrahydro-2-(1H)-pyrimidone (2 ml) was evacuated and filled with argon for five times. A mixture of 2-(di-t-butylphosphino)biphenyl (16 mg, 0.05 mmol), tris(dibenzylideneacetone)dipalladium(0) chloroform complex (9 mg, 0.01 mmol) and potassium fluoride (172 mg, 2.97 mmol) was added to the solution. After stirring for 5 min under an argon atmosphere water (0.19 mL, 10.7 mmol) and hexamethyldisilane (0.14 ml, 0.71 mmol) were added and the reaction mixture was stirred for 23 h at 100° C. Further hexamethyldisilane (0.14 mL, 0.71 mmol) was added and stirring was continued at 100° C. for another 24 h. The mixture was diluted with dichloromethane (10 ml) and washed with aqueous sodium carbonat (half saturated) and water. Drying over sodium sulfate and purification by chromatography ($SiO_2$, heptane:ethyl acetate:dichloromethane=60:20:20 to 30:50:20) afforded the title compound (25 mg, 13%) as a white solid. MS: m/e=330.1 [M]$^+$.

EXAMPLE 69

10-Chloro-3-(methoxy-carbonyl)-9H-imidazo[1,5-a][1,2,4]triazolo[1,5-d][1,4]benzodiazepine To a suspension of 3-bromo-10-chloro-9H-imidazo[1,5-a][1,2,4]triazolo[1,5-d][1,4]-benzodiazepine (200 mg, 0.59 mmol) in methanol (2 mL) and THF (2 mL) was added under an argon atmosphere palladium(II) acetate (13 mg, 0.06 mmol), triphenylphosphine (62 mg, 0.24 mmol) and sodium acetate (5 mg, 0.06 mmol). The white suspension was evacuated and filled with carbon monoxide for 5 times and stirred for 18 h at 65° C. under a carbon monoxide atmosphere. The suspension went into solution. Stirring was continued for further 3 d at 65° C. Further sodium formate (61 mg, 0.89 mmol) and bis(triphenylphosphine)palladium(II) chloride (21 mg, 0.03 mmol) were added and the mixture was stirred for 18 h at 60° C. under a carbon monoxide atmosphere. It was filtered over hyflo® and concentrated in vacuo. Purification by chromatography ($SiO_2$, heptane:ethyl acetate:dichloromethane=60:20:20 to 30:50:20) afforded the title compound (89 mg, 47%) as a white solid. MS: m/e=316.1 [M+H]$^+$.

EXAMPLE 70

10-Chloro-3-(propa-1,2-dienyl)-9H-imidazo[1,5-a][1,2,4]triazolo[1,5-d][1,4]benzodiazepine a) 10-Chloro-3-(3-diethylamino-prop-1-ynyl)-9H-imidazo[1,5-a][1,2,4]triazolo[1,5-d][1,4]benzodiazepine To a solution of 3-bromo-10-chloro-9H-imidazo[1,5-a][1,2,4]triazolo[1,5-d][1,4]-benzodiazepine (600 mg, 1.78 mmol) in THF (40 mL) were added 3-diethylamino-1-propyne (317 mg, 2.86 mmol), bis(triphenylphosphin)-palladium(II) dichloride (63 mg, 0.09 mmol) triphenylphosphine (14 mg, 0.05 mmol) and triethylamine (890 µL, 6.41 mmol). The resulting mixture was stirred for 15 min at ambient temperature before adding copper(I) bromide (3 mg, 0.02 mmol). After heating to reflux for 15 h the mixture was poured onto water (20 mL) and was extracted with ethyl acetate. Drying over sodium sulfate, concentration and purification by chromatography ($SiO_2$, ethyl acetate:methanol=80:20) afforded the title compound (440 mg, 67%) as an off-white solid. MS: m/e=367.0 [M+H]$^+$.

b) 10-Chloro-3-(propa-1,2-dienyl)-9H-imidazo[1,5-a][1,2,4]triazolo[1,5-d][1,4]benzodiazepine 10-Chloro-3-(3-diethylamino-prop-1-ynyl)-9H-imidazo[1,5-a][1,2,4]triazolo[1,5-d][1,4]benzodiazepine (200 mg, 0.54 mmol) was dissolved in dioxane (2 mL) tris(dibenzylideneaceton)dipalladium chloroform complex (14 mg, 0.01 mmol) and tris(pentafluorophenyl)phosphine (58 mg, 0.11 mmol) were added. The resulting brown solution was heated to reflux for 26 h. The reaction mixture was poured onto water (30 mL) and was extracted with dichloromethane. The combined organic layers were dried over sodium sulfate and concentrated. Purification by chromatography ($SiO_2$, ethyl acetate:dichloromethane:methanol=90:9:1) afforded the title compound (14 mg, 9%) as a yellow solid. MS: m/e=295.0 [M]$^+$.

EXAMPLE 71

3-(Acetyl-methyl-amino)-10-chloro-9H-imidazo[1,5-a][1,2,4]triazolo[1,5-d][1,4]benzodiazepine 3-(Acetyl-amino)-10-chloro-9H-imidazo[1,5-a][1,2,4]triazolo[1,5-d][1,4]benzodiazepine (840 mg, 2.67 mmol) was dissolved in DMF (16 mL) and potassium hexamethyldisilane (0.91 M in THF, 3.80 mL, 3.47 mmol) was added. After stirring for 45 min at ambient temperature methy iodide (217 µL, 3.47 mmol) was added and stirring of the resulting mixture continued for 2 h. The reaction mixture was separated between aqueous sodium carbonate (saturated) and ethyl acetate. The organic layer was washed with water, dried over sodium sulfate and concentrated. Purification by chromatography (SiO$_2$, heptane:ethyl acetate:dichloromethane=60:20:20 to 30:50:20) afforded the title compound (234 mg, 27%) as a white solid. MS: m/e=329.1[M]$^+$.

EXAMPLE 72

10-chloro-3-cyclopropylamino-9H-imidazo[1,5-a][1,2,4]triazolo[1,5-d][1,4]benzodiazepine To a solution of 10-chloro-3-fluoro-9H-imidazo[1,5-a][1,2,4]triazolo[1,5-d][1,4]benzodiazepine (200 mg, 0.73 mmol) in DMSO (2 mL) in a sealed tube was added cyclopropylamine (254 pi, 3.63 mmol) and the mixture was stirred for 90 min at 180° C. (microwave). Potassium carbonate (300 mg, 2.17 mmol) was added and stirring was continued for further 60 min at 180° C. (microwave). The reaction mixture was diluted with ethyl acetate (20 mL), washed with aqueous sodium carbonate (saturated) and extracted with ethyl acetate. Drying over sodium sulfate and purification by chromatography (SiO$_2$, heptane:ethyl acetate:dichloromethane=40:40:20 to 10:70:20) afforded the title compound (15 mg, 7%) as a brown solid. MS: m/e=313.1 [M+H]$^+$.

The invention claimed is:

1. A compound comprising a halogen substituted imidazo[1,5-a][1,2,4]triazolo[1,5-d][1,4]benzodiazepine of formula I

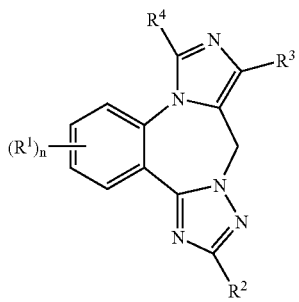

wherein

R$^1$ is hydrogen, halogen, lower alkyl, Si(CH$_3$)$_3$, lower alkyl substituted by halogen, lower alkoxy, lower alkoxy substituted by halogen, lower alkenyl, lower alkenyloxy, ON, bicyclo[2.2.1]hept-5-en-2-yl, aryl which is optionally substituted by lower alkyl, amino or lower alkoxy, or is aryloxy, heteroaryl, benzo[1,3]dioxolyl, cycloalkyl, heterocycloalkyl, —O(CH$_2$)$_m$OH, —CO(O)-lower alkyl, —N(R')$_2$ or —C≡C—R";

R' is hydrogen, lower alkyl, cycloalkyl, —C(O)-lower alkyl, —C(O)-cycloalkyl, —S(O)$_2$-lower alkyl, or aryl which is unsubstituted or substituted by one or two substituents selected from the group consisting of halogen and lower alkyl substituted by halogen;

R" is hydrogen, —Si(CH$_3$)$_3$, lower alkyl, cycloalkyl or —(CH$_2$)$_m$—O-lower alkyl;

R$^2$ is hydrogen, methyl or aryl;

R$^3$ is halogen;

R$^4$ is hydrogen or halogen;

n is 1 or 2; and m is 1, 2 or 3;

or a pharmaceutically acceptable acid addition salt thereof.

2. A compound of claim 1 comprising formula IA

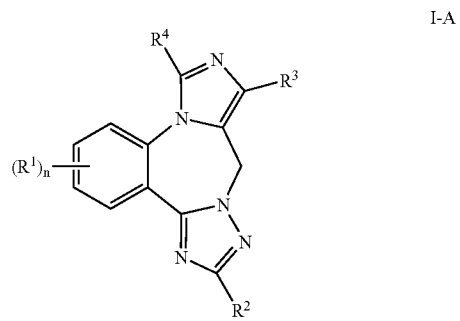

wherein

R$^1$ is hydrogen, halogen, lower alkyl, lower alkyl substituted by halogen, lower alkoxy, lower alkoxy substituted by halogen, lower alkenyl, lower alkenyloxy, CN, aryl, aryloxy, heteroaryl, cycloalkyl, heterocycloalkyl, —O(CH$_2$)$_m$OH, —N(R')$_2$ or —C≡C—R";

R' is hydrogen, lower alkyl, —C(O)-lower alkyl, —C(O)-cycloalkyl, —S(O)$_2$-lower alkyl, or aryl which is unsubstituted or substituted by one or two substituents selected from the group consisting of halogen and lower alkyl substituted by halogen;

R" is hydrogen, —Si(CH$_3$)$_3$, lower alkyl, cycloalkyl or —(CH$_2$)$_m$—O-lower alkyl;

R$^2$ is hydrogen, methyl or aryl;

R$^3$ is halogen;

R$^4$ is hydrogen or halogen;

n is 1 or 2; and m is 1, 2 or 3;

or a pharmaceutically acceptable acid addition salt thereof.

3. A compound of claim 1, wherein R$^3$ chlorine.

4. A compound of claim 3, wherein R$^2$ is hydrogen.

5. A compound of claim 4, selected from the group consisting of:

10-chloro-9H-imidazo[1,5-a][1,2,4]triazolo[1,5-d][1,4]benzodiazepine, 10-chloro-3-fluoro-9H-imidazo[1,5-a][1,2,4]triazolo[1,5-d][1,4]benzodiazepine, 10-chloro-3-methoxy-9H-imidazo[1,5-a][1,2,4]triazolo[1,5-d][1,4]benzodiazepine, 10-chloro-3-ethoxy-9H-imidazo[1,5-a][1,2,4]triazolo[1,5-d][1,4]benzodiazepine, 10-chloro-3-(2-fluoro-ethoxy)-9H-imidazo[1,5-a][1,2,4]triazolo[1,5-d][1,4]benzodiazepine, 10-chloro-3-(2,2-difluoro-ethoxy)-9H-imidazo[1,5-a][1,2,4]triazolo[1,5-d][1,4]benzodiazepine, 10-chloro-3-(2,2,2-trifluoro-ethoxy)-9H-imidazo[1,5-a][1,2,4]triazolo[1,5-d][1,4]benzodiazepine, and 10-chloro-3-vinyloxy-9H-imidazo[1,5-a][1,2,4]triazolo[1,5-d][1,4]benzodiazepine.

6. A compound of claim 4, selected from the group consisting of:

10-chloro-3-methylamino-9H-imidazo[1,5-a][1,2,4]triazolo[1,5-d][1,4]benzodiazepine, 10-chloro-3-dimethylamino-9H-imidazo[1,5-a][1,2,4]triazolo[1,5-d][1,4]benzodiazepine, 3-benzylamino-10-chloro-9H-imidazo[1,5-a][1,2,4]triazolo[1,5-d][1,4]benzodiazepine, 10-chloro-3-thiomorpholin-4-yl-9H-imidazo[1,5-a][1,2,4]triazolo[1,5-d][1,4]benzodiazepine, 10-chloro-3-imidazol-1-yl-9H-imidazo[1,5-a][1,2,4]triazolo[1,5-d][1,4]benzodiazepine,
3-acetylamino-10-chloro-9H-imidazo[1,5-a][1,2,4]triazolo[1,5-d][1,4]benzodiazepine,
3,10-dichloro-9H-imidazo[1,5-a][1,2,4]triazolo[1,5-d][1,4]benzodiazepine, and
3-bromo-10-chloro-9H-imidazo[1,5-a][1,2,4]triazolo[1,5-d][1,4]benzodiazepine.

7. A compound of claim 4, selected from the group consisting of:
10-chloro-3-methyl-9H-imidazo[1,5-a][1,2,4]triazolo[1,5-d][1,4]benzodiazepine,
10-chloro-3-ethynyl-9H-imidazo[1,5-a][1,2,4]triazolo[1,5-d][1,4]benzodiazepine,
10-chloro-3-prop-1-ynyl-9H-imidazo[1,5-a][1,2,4]triazolo[1,5-d][1,4]benzodiazepine,
10-chloro-3-cyclopropylethynyl-9H-imidazo[1,5-a][1,2,4]triazolo[1,5-d][1,4]benzodiazepine,
10-chloro-3-ethyl-9H-imidazo[1,5-a][1,2,4]triazolo[1,5-d][1,4]benzodiazepine,
10-chloro-3-cyclopropyl-9H-imidazo[1,5-a][1,2,4]triazolo[1,5-d][1,4]benzodiazepine,
10-chloro-3-difluoromethyl-9H-imidazo[1,5-a][1,2,4]triazolo[1,5-d][1,4]benzodiazepine,
3-benzyl-10-chloro-9H-imidazo[1,5-a][1,2,4]triazolo[1,5-d][1,4]benzodiazepine, and
10-chloro-3-phenyl-9H-imidazo[1,5-a][1,2,4]triazolo[1,5-d][1,4]benzodiazepine.

8. A compound of claim 4, selected from the group consisting of:
10-chloro-3-cyano-9H-imidazo[1,5-a][1,2,4]triazolo[1,5-d][1,4]benzodiazepine,
10-chloro-3-(pyridin-3-yl)-9H-imidazo[1,5-a][1,2,4]triazolo[1,5-d][1,4]benzodiazepine,
10-chloro-3-propyl-9H-imidazo[1,5-a][1,2,4]triazolo[1,5-d][1,4]benzodiazepine,
3-butyl-10-chloro-9H-imidazo[1,5-a][1,2,4]triazolo[1,5-d][1,4]benzodiazepine,
10-chloro-3-vinyl-9H-imidazo[1,5-a][1,2,4]triazolo[1,5-d][1,4]benzodiazepine,
10-chloro-3-(methoxy-carbonyl)-9H-imidazo[1,5-a][1,2,4]triazolo[1,5-d][1,4]benzodiazepine,
10-chloro-3-(propa-1,2-dienyl)-9H-imidazo[1,5-a][1,2,4]triazolo[1,5-d][1,4]benzodiazepine,
3-(cyclopropanecarbonyl-amino)-10-chloro-9H-imidazo[1,5-a][1,2,4]triazolo[1,5-d][1,4]benzodiazepine and
10-chloro-3-cyclopropylamino-9H-imidazo[1,5-a][1,2,4]triazolo[1,5-d][1,4]benzodiazepine.

9. A compound of claim 3, wherein $R^2$ is methyl.

10. A compound of claim 9, selected from the group consisting of
3,10-dichloro-6-methyl-9H-imidazo[1,5-a][1,2,4]triazolo[1,5-d][1,4]benzodiazepine,
3-bromo-10-chloro-6-methyl-9H-imidazo[1,5-a][1,2,4]triazolo[1,5-d][1,4]benzodiazepine,
10-chloro-3-ethynyl-6-methyl-9H-imidazo[1,5-a][1,2,4]triazolo[1,5-d][1,4]benzodiazepine,
10-chloro-3-cyclopropyl-6-methyl-9H-imidazo[1,5-a][1,2,4]triazolo[1,5-d][1,4]benzodiazepine and
10-chloro-3-cyano-6-methyl-9H-imidazo[1,5-a][1,2,4]triazolo[1,5-d][1,4]benzodiazepine.

11. A compound of claim 1, wherein $R^3$ is bromine.

12. A compound of claim 11, selected from the group consisting of
10-bromo-9H-imidazo[1,5-a][1,2,4]triazolo[1,5-d][1,4]benzodiazepine and
10-bromo-3-fluoro-9H-imidazo[1,5-a][1,2,4]triazolo[1,5-d][1,4]benzodiazepine.

13. A compound of claim 1, wherein $R^3$ iodine.

14. A compound of claim 13, which is 3-chloro-10-iodo-9H-imidazo[1,5-a][1,2,4]triazolo[1,5-d][1,4]benzodiazepine.

15. A compound of claim 1, wherein $R^1$ is hydrogen, halogen, lower alkyl, lower alkyl substituted by halogen, lower alkenyl, cycloalkyl, or —C≡C—R".

16. A compound of claim 1, wherein $R^1$ is lower alkoxy, lower alkoxy substituted by halogen, lower alkenyloxy, aryloxy, or —O(CH$_2$)$_m$OH.

17. A compound of claim 1, wherein $R^1$ is aryl which is optionally substituted by lower alkyl, amino or lower alkoxy, or is bicyclo[2.2.1]hept-5-en-2-yl.

18. A compound of claim 1, wherein $R^1$ is heteroaryl, benzo[1,3]dioxolyl, or heterocycloalkyl.

19. A compound of claim 1, wherein $R^1$ is Si(CH$_3$)$_3$, CN, —CO(O)-lower alkyl, or —N(R')$_2$.

20. A compound of claim 1, wherein $R^2$ is hydrogen.

21. A compound of claim 1, wherein $R^2$ is methyl.

22. A compound of claim 1, wherein $R^2$ is aryl.

23. A pharmaceutical composition comprising a compound for formula I wherein
$R^1$ is hydrogen, halogen, lower alkyl, Si(CH$_3$)$_3$, lower alkyl substituted by halogen, lower alkoxy, lower alkoxy substituted by halogen, lower alkenyl, lower alkenyloxy, ON, bicyclo[2.2.1]hept-5-en-2-yl, aryl which is optionally substituted by lower alkyl, amino or lower alkoxy, or is aryloxy, heteroaryl, benzo[1,3]dioxolyl, cycloalkyl, heterocycloalkyl, —O(CH$_2$)$_m$OH, —CO(O)-lower alkyl, —N(R')$_2$ or —C≡C—R";

R' is hydrogen, lower alkyl, cycloalkyl, —C(O)-lower alkyl, —C(O)-cycloalkyl, —S(O)$_2$-lower alkyl, or aryl which is unsubstituted or substituted by one or two substituents selected from the group consisting of halogen and lower alkyl substituted by halogen;

R" is hydrogen, —Si(CH$_3$)$_3$, lower alkyl, cycloalkyl or —(CH$_2$)$_m$—O-lower alkyl;

$R^2$ is hydrogen, methyl or aryl;

$R^3$ is halogen;

$R^4$ is hydrogen or halogen;

n is 1 or 2; and m is 1, 2 or 3;

or a pharmaceutically acceptable acid addition salt thereof and a pharmaceutically acceptable carrier.

24. A process for preparation of compounds of formula I

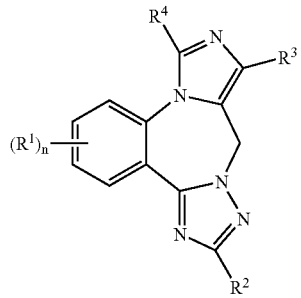

wherein
R¹ is hydrogen, halogen, lower alkyl, Si(CH₃)₃, lower alkyl substituted by halogen, lower alkoxy, lower alkoxy substituted by halogen, lower alkenyl, lower alkenyloxy, CN, bicyclo[2.2.1]hept-5-en-2-yl, aryl which is optionally substituted by lower alkyl, amino or lower alkoxy, or is aryloxy, heteroaryl, benzo[1,3]dioxolyl, cycloalkyl, heterocycloalkyl, —O(CH₂)ₘOH, —CO(O)-lower alkyl, —N(R')₂ or —C≡C—R";

R' is hydrogen, lower alkyl, cycloalkyl, —C(O)-lower alkyl, —C(O)-cycloalkyl, —S(O)₂-lower alkyl, or aryl which is unsubstituted or substituted by one or two substituents selected from the group consisting of halogen and lower alkyl substituted by halogen;

R" is hydrogen, —Si(CH₃)₃, lower alkyl, cycloalkyl or —(CH₂)ₘ—O-lower alkyl;

R² is hydrogen, methyl or aryl;
R³ is halogen;
R⁴ is hydrogen or halogen;
n is 1 or 2; and
m is 1, 2or 3;
which process comprises
reacting a compound of formula

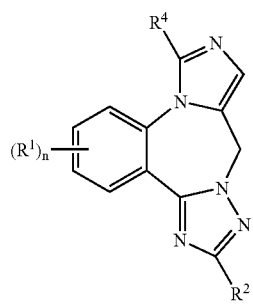

with a halogenating agent to produce a compound of formula

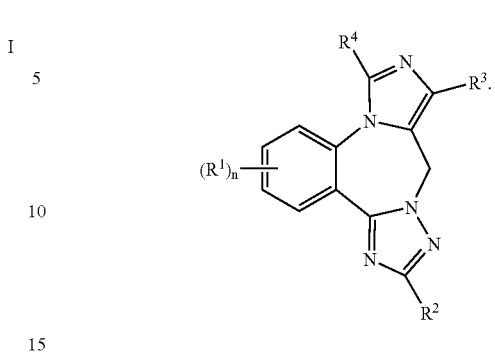

25. A method of enhancing cognition or treating a disorder selected from the group consisting of cognitive disorders, anxiety, Alzheimer's disease, and schizophrenia comprising administering to an individual a therapeutically effective amount of a compound of formula I

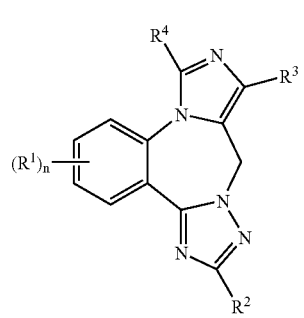

wherein
R¹ is hydrogen, halogen, lower alkyl, Si(CH₃)₃, lower alkyl substituted by halogen, lower alkoxy, lower alkoxy substituted by halogen, lower alkenyl, lower alkenyloxy, CN, bicyclo[2.2.1]hept-5-en-2-yl, aryl which is optionally substituted by lower alkyl, amino or lower alkoxy, or is aryloxy, heteroaryl, benzo[1,3]dioxolyl, cycloalkyl, heterocycloalkyl, —O(CH₂)ₘOH, —CO(O)-lower alkyl, —N(R')₂ or —C≡C—R";

R'is hydrogen, lower alkyl, cycloalkyl, —C(O)-lower alkyl, —C(O)-cycloalkyl, —S(O)₂-lower alkyl, or aryl which is unsubstituted or substituted by one or two substituents selected from the group consisting of halogen and lower alkyl substituted by halogen;

R" is hydrogen, —Si(CH₃)₃, lower alkyl, cycloalkyl or —(CH₂)ₘ—O-lower alkyl;

R² is hydrogen, methyl or aryl;
R³ is halogen;
R⁴ is hydrogen or halogen;
n is 1 or 2; and
m is 1, 2or 3;
or a pharmaceutically acceptable acid addition salt thereof.

26. The method of claim 25 wherein the disorder is Alzheimer's disease.

* * * * *